United States Patent [19]

Mandel et al.

[11] Patent Number: 5,644,045

[45] Date of Patent: Jul. 1, 1997

[54] X-LINKED ADRENOLEUKODYSTROPHY GENE AND CORRESPONDING PROTEIN

[75] Inventors: Jean-Louis Mandel, Schiltigheim; Patrick Aubourg, Sceaux; Jean Mosser; Claude Sarde, both of Strasbourg, all of France

[73] Assignee: Institut National de la Sante et de la Recherche Medicale, Paris Cedex, France

[21] Appl. No.: 136,277

[22] Filed: Oct. 15, 1993

[51] Int. Cl.$^6$ .................................................. C07H 21/04
[52] U.S. Cl. ........................... 536/23.5; 536/23.1; 935/9
[58] Field of Search .................. 536/23.1, 23.5; 514/44; 935/9

[56] References Cited

U.S. PATENT DOCUMENTS 5,227,170  7/1993  Sullivan .................................. 424/450

OTHER PUBLICATIONS

By J. Mosser et al., "Putative X–linked adrenoleukodystrophy gene shares unexprected homology with ABE transporters", Feb. 25, 1993, pp. 726–730, vol. 361, Nature.

By R. Feil et al., "Adrenoleukodystrophy: a Complex Chromosomal Rearrangement in the Xq28 Red/Green–Color–Pigment Gene Region Indicates Two Possible Gene Localizations", 1991, vol. 49, pp. 1361–1371, American Journal of Human Genetics.

By P. Aubourg et al., "Frequent Alterations of Visual Pigment Genes in Adrenoleukodystrophy", 1988, pp. 408–413, vol. 42, American Journal of Genetics.

By H. Moser et al., "Adrenoleukodystrophy: Phenotypic Variability and Implications for Therapy", 1992, pp. 645–664.

D Valle et al (1993) Nature 361:682–683.

Primary Examiner—Bruce R. Campell
Attorney, Agent, or Firm—Young & Thompson

[57] ABSTRACT

The cDNA and genomic DNA sequences encoding the human adrenoleukodystrophy protein are provided. Mutations of the adrenoleukodystrophy protein cause adrenoleukodystrophy or adrenomyelopathy.

5 Claims, 13 Drawing Sheets

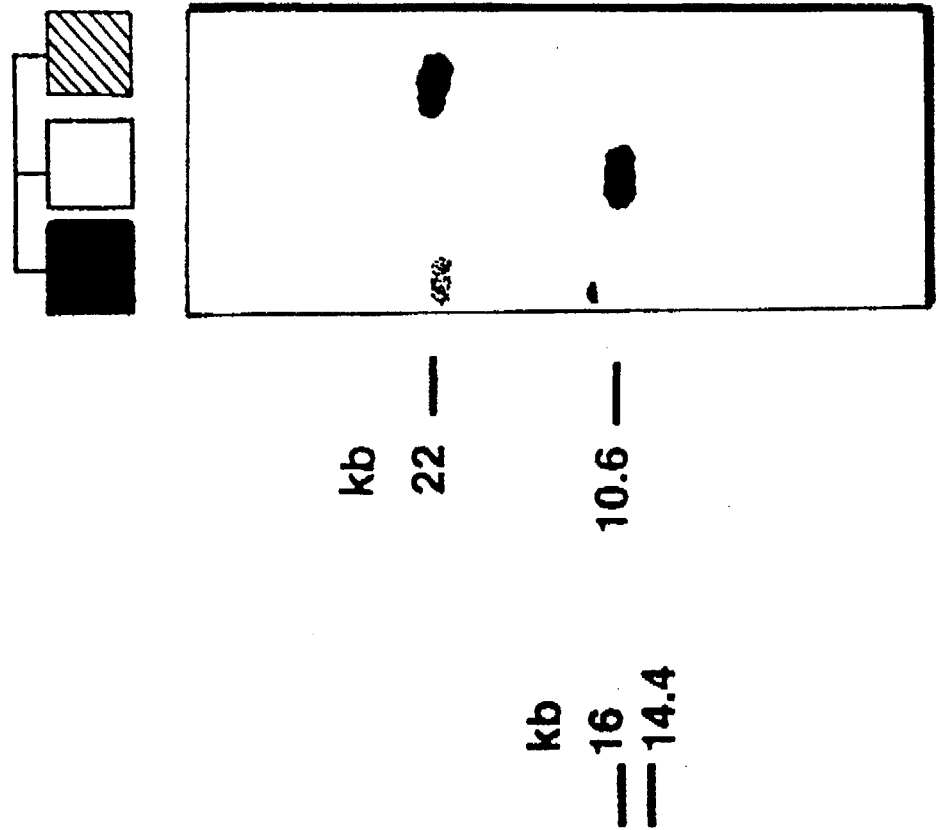
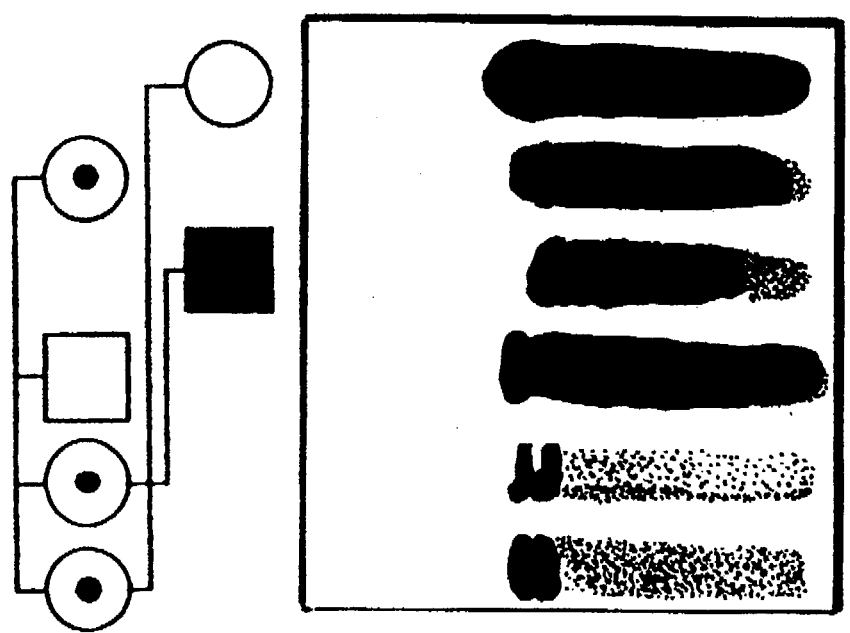

```
PMP70  MAAFSKYLTARNSSLAGAAFLLCLLHKRRA--LGL--HGKKSGK--PPLQ--NNEKEG                    1- 52
        : .:. .  :  :::. ... :. .  .:  :     :. : .
ALDP   MPVLSRPRPWRGNTLKRTAVLLALAAYGAHKVYPLVRQCLAPARGLQAPAGEPTQEASGV                  1- 60

PMP70  KKERAVVDKVFFSRLIQILKIMVPRTFCKETGYLVLIAVMLVSRTYCDVWMIQNGTLIES                  53-112
       .: ::.  :.:  : .:. ::: ::.:. :  ::.:::  . ..
ALDP   AAAKAGMNRVFLQRLLWLLRLLFPRVLCRETGLLALHSAALVSRTFLSVYVARLDGRLAR                 61-120

PMP70  GIIGRSRKDFKRYLLNFIAAMPLISLVNNFLKYGLNELKLCFRVRLTKYLYEEYLQAFTY                 113-172
       :   .: : ::: ::. . :   :.   :. :: .: .  :  ..   :   :  ::
ALDP   CIARKDPRAFGWQLLQWLLIALPATFVNSAIRYLEGQLALSFRSRLVAHAYRLYFSQQTY                121-180

PMP70  YKKGNLDNRIANPDQLLTQDVEKFCNSVVDLYSNLSKPFLDIVLYIFKLTSAIGAQGPA-                 173-231
       :     .:.:   .:.:: .::: ::  .   : :.:::::. .:. ::::::
ALDP   YRVSNMDGRLRNPDQSLTEDVVAFAASVAHLYSNLTKPLLDVAVTSYTLLRAARSRGAGT                181-240

PMP70  ---SMMAYLVV--SGLFLTRLRRPIGKMTITEQKYEGEYRYVNSRLITNSEEIAFYNGNK                 232-286
          :. . ..   ..  .  : :::::::::::.:..  :::::::::.
ALDP   AWPSAIAGLVVFLTANVLRAFSPKFGELVAEEARRKGELRYMHSRVVANSEEIAFYGGHE                241-300

PMP70  REKQTVHSVFRKLVEHLHNFILFRFSMGFIDSIIAKYLATVVGYLVVSRPFL-------                 287-338
       .: . :..  :  ..  ::.  :.: . ::  :.::::  :: .:.  :::
ALDP   VELALLQRSYQDLASQINLILLERLWYVMLEQFLMKYVWSASGLLMVAVPIITATGYSES                301-360

PMP70  --DLSHPRHLKSTHSELL---EDYYQSGRMLLR-MSQALGRIVLAGREMTRLAGFTARIT                339-392
         : ::.  :: :..::.   :  :.  : :  :. ::.::.:::: :.::.:::::..
ALDP   DAEAVKKAALEKKEEELVSERTEAFTIARNLLTAAADAIERIMSSYKEVTELAGYTARVH                361-420
```

FIG. 4B

```
PMP70  ELMQVLKDLNHGKYERTM-VSQQEK-----GIEGVQVIPLIPGAGEIIADNIIKFDHVP              393-446
       ::  ::  :::  ::  ::        :  :::::    ::::  :
ALDP   EMFQVFEDVQRCHFKRPRELEDAQAGSGTIGRSGVRVEGPLKIRGQVVDVEQGIICENIP            421-480

PMP70  LATPNGDVLIRDLNFEVRSGANVLICGPNGCGKSSLFRVLGELWPLFGGRLTKPERRKLF             447-506
       :  ::: :::    :  ::::::::::::::::::::  :: ::: ::
ALDP   IVTPSGEVVVASLNIRVEEGMHLLITGPNGCCKSSLFRILGGLWPTYGGVLYKPPPQRMF             481-540

PMP70  YVPQRPYMTLGTLRDQVIYPDGREDQKRKGISDLVQKEYLDNVQLGHILEREGGWDSVQD             507-566
       : :::: ::  :::::::::  :  :    :: :  ::: :::::::::::
ALDP   YIPQRPYMSVGSLRDQVIYPDSVEDMQRKGYSEQDLEAILDVVHLHHILQREGGWEAMCD             541-600

PMP70  WMDVLSGGEKQRMAMARLFYHKPQFAILDECTSAVSVDVEGYIYSHCRKVGITLFTVSHR             567-626
       :::::::::::::  :::::::: ::::::::::::::  :    ::::::::
ALDP   WKDVLSGGEKQRIGMARMFYHRPKYALLDECTSAVSIDVEGKIFQAAKDAGIALLSITHR             601-660

PMP70  KSLWKHHEYYLHMDGRGNYEFKQITEDTVEFGS---------------------------             627-659
       :::::  :::  :: ::  ::  ::  ::
ALDP   PSLWKYHTHLLQFDGEGGWKFEKLDSAARLSLTEEKQRLEQLAGIPKMQRRLQELCQIL              661-720

PMP70  ------------------------                                                  
ALDP   GEAVAPAHVPAPSPQGPGGLQGAST                                                721-745
```

```
                        EXON 1 -          -(1286)- AG
    gtggggcaggttggggtgccgggcacggagggaagcgtgtggcagggagg
    ccgggggcaggcagccgtgagcggtggggacagtctggggcgggccggg
    gctgatgccaaaggtgtgggcaggccatgggagagccgggctgggtggg
    --------------------/# 2900 bp/--------------------
    cacccaatcgtaacctctggctctcggccttctgatggccaccatggcac
    agcgtgtgtgagtggcactgggagaccctgaccatcgccccacgggagc
    tgcccctgtgcatggccaggaagcctctctgtgtctgtcaccccgcag
    GT -(1287)-          - EXON 2 -        -(1467)- AG
    gtgagacccagggctccaagaggatccaggccaggggcctgtcccccata
    ccgctgggtgctgagctcacgagggcccaactcagccagcccgccgccca
    cttctgctgccggggccaccgaggccctgctgccagccttgatgctttca
    --------------------/# 6600 bp/--------------------
    gcacatagagagaaagagagagagagctggttgccccggcaccatttgca
    gaagagcctcgcctttctctccagcggctcattttgactttccgctgtc
    tctgccctgccctccccgcccgccacccacccctctggggctttgcag
    AT -(1468)-          - EXON 3 -        -(1610)- AG
    gtaccctggcccagccccacccttgccatccttgccatgcttctctccc
    tgcaactggcaggggctgagccagggtcaccctccctcag
    GT -(1611)-          - EXON 4 -        -(1729)- AG
    gtaaggctgtcccctccctatgagtgacccgccctgctgctgctgcag
    gtgctgacctgctgccccagctcctctattcccgctccctcactcaggg
    acctccatgtgcttctggcccatcccagtccacccaggacgggagggctg
    --------------------/# 350 bp/--------------------
    ctggaccacaggctgctggtcaggaaccagctggcatgctgccagggatg
    ggaatgagggcgtgcagccaggggcacgcagactccccagaatgcagagg
    ggtcgccaccactccctctccaccccagccccgctgtgctgtctctgcag
    GC -(1730)-          - EXON 5 -        -(1840)- GG
    gtaggtccagcggggagggcgccagccacgcacatatgcaagcctcagcc
    cttggcttcccgcctgtctgtgctggcaacagccattgtccctagatgta
    cgtggcaggtgggccaaggtcaaggtgagagaccaacgtgtctctgactg
    --------------------/# 3000 bp/--------------------
    tcccccaggccctgctgtcccttatcaagagatcaagaatggcctgcgtg
    ctggcctcgggcattgggagcctctcaaggctggtcaggaggccataggg
    tacgggaaggggcctgcgctctctggcgtcagcggctgttgcccctgcag
    GT -(1841)-          - EXON 6 -        -(1986)- AG
    gtaaggaagcccgtgcgcctctcctccacctcttcctgcctgtgcgctca
    cacatggcttcctgcagaggcccaggaagtggtgaagagtcagcacctca
    ggagaggacactgaggcactgtccccagagccagagacgggctgtggttc
    ctgctccctccaaacccgcccgatccactgccctgttttggatctgtgtg
    gggtgtgtgcacgggcggcgatgtgagcgtgtggatgcgtgtgagcgtgg
    catgtggacactgcctgggaggcgcagagtatcttgggggaggcagagcc
    ggcccttccctccgtggacacccagctttcccacag
    GC -1987)-           - EXON 7 -        -(2132)- AG
    gtaggaggcctggggctggcagccacccttgtcccaccctggcctctcc
    cttggcctccaggagtgaagattacctcaacatccagagtctaaagtgc
    caggtgccacggggcggggcagaggctgctaccaggaggaccaacacca
    --------------------/# 1700 bp/--------------------
    atgattaatgcctgtcagacagacaaggacgcagaggcacaggggccctg
    tcgtcacagctagctcattcccgcagctcccccagctccccggctggccc
    ccgggtctgggtgctggtggaactgagccaagaccattgccccgcctag
    GT -(2133)-          - EXON 8 -        -(2218)- AG
    gtgagcactccggaccggcaggctccctggggtcccctggaaggggaagt
    agcagctgtggggaggcctgggctcagtggagcctgagccgggctggggt
    gttgggccctggagggtgcacagactctcctctcggcccggaccccag
    GC -(2219)-          - EXON 9 -        -(2344)- TG
    gtaggtgccctgtctccctgcctggggtcggtgggagtgcctgcctgagg
    ggaggaggtggcctggcgggccggcagcagcaggcggctgtcatcagca
    gcccccgtgccgtgccctgaccctgtccctctcctggcag
    GA -(2345)-          - EXON 10
```

FIG. 6

```
GCGGAGCGGACGGCGCCTGGTGCCCCGGGGAGGGGCGCCACCGGGGAGGAGGAGGA
GGAGAAGGTGGAGAGGAAGAGAGACAGGCACTGACAGACAGGAGACGCGCTCTGACCTGCCCCTGACCTC
AGGGGCCAAGGGCACTGACAGACAGGAGACAGGAGACCCTCTCACTTGGCTGCCCGAAGA
GGCCGCGACCCTGAGGGCCCTGAGCCCACCGACACCCAGGGCCCAGCACCACCACCCCGGGG
GCCTAAAGCGACAGTCTCAGGGCCATCGCAAGGTTCCAGTTGCCTAGACAACAGCCC
AGGGTCAGAGCAACAACAATCCTTCCAGCCAGTCTGCCTCAACTGCTGCCCAGCCACCAGCC
CAGTCCCTACGCGCAGCCAGCCAGTGACATGCCGGTGCTCTCCAGCGCCCCGCCCTG
GCGGGGAACACGCTGAAGCGCACGGCCGTGCTCCTGGCCCTCGCGGCCTATGGAGCCCA
CAAAGTCTACCCCCTTGGTGCGCCAGTGCCTGGCCCCCGGCCAGGGGTCTTCAGGCGCCGC
CGGGGAGCCAGGCCCACGCCAGGAGGCCTCCGGGGTCGCGGCGCAAAGCTGGCATGAACCGGGT
ATTCCTGCAGCGGCTCCTGTGCTCCTGGCTCCCCGGTGTTCCCCGGTCCTGTGCCGGA
GACGGGCTGCTGGCCCTGGACGGAAGGCTGGCTCCTGGTGAGCGCCCGCCACCTTCCTGTCTCGGTGTA
TGGTGGCCCGCTGCAGTCGTGCTGAGTGCCCAGTGGCTCCTGCCCCTGCTACCTTCGTCAACAGTGC
CATCCGTTACCTGGAGGGCCAACTGGCCCTGTTCCGCAGCCGTCTGGCCAGCCGTCTGGTGGCCCACGC
CTACCGCCTCTACTTCTCCCAGCAGACCAGTCCAGGAGACGTGGGCCTTTGCGCCTCTGTGCCCA
TCGCAACCCTGACCAAGCCACTCCTGACGACGTGCTGACTTCCTACACCCTGCT
TCGGGCGCCCCGCCTCCCGTGGAGCCTCCCGGCACAGCCTGCCCTCGCAAGTTCGGGAGCTGGTGGC
GGTGTTCCTCACGCCAACTGTCTGCCTACATGCGCTACACTGCACTGCGTGTGGTGGCCAACTC
AGAGGAGGCGCGGCGAAGGGGAGCTGCGCTACATGCCCATGAGgtggcaggagccgggacgga
GGAGGAGATCGCCTTCTATGGGGCCAAAGgtgtgggcaggcacggggaggagcagtctgg
gcgcggcccggggctgatgccaaaggtgggcaggcagtgggcaggagccgggctggggtgg
g
```

FIG. 7A cacccaatcgtaacctctggctctccggcctttctgatggccaccatggcacagcgtgtg
agtggcactgggagaccctgaccatcgcccccacggagctgccctgtgcatggccagg
aagccctctctgtgtctgtcaccccccgcagGTGGAGCTGGCCCCTGCTACAGCGCTCCTAC
CAGGACCTGGCCTCGCAGATCAACCTCATCCTTCTGAACGCCTGTGGTATGTTATGCTG
GAGCAGTTCCTGCCACTGGTATGTGTGGAGCGCCTCGGGCCTCTGCTCATGGTGGCTGTCCCC
ATCATCACTGCCACTGCCACTGGCTACTGCAGAGTCAGgtgagacccaggctccaagaggatccag
gccaggggcctgtccccccataccgctgggtgctgagctcacgagggcccaactcagccag
cccgccgcccacttctgctgccgggccaccgaggcccctgctgccagcctgcttgatgcttttc
a gcacatagagagagaaagagagagagagctgttgccccggcaccatttgcagaagagccctc
gccttctctccagcggctcattttgactttcgctgtcctgccctgccctcccccgc
cccgccaccccactccctgggctttgcagATGCAGAGGCCGTGAAGAGGCCGTGAAGAAGGCAGCCTTGG
AAAGAAGGAGGAGGAGCTGGTGCAGATGCCATTGAGCGGATCATGTCGTGTACAAGGAGgtaccc
TCCTGACACAGCGGCTGCCCCACCCTTGCCATCCTTGCCATCTTTCTCCCTGCAACTGGCAGGGCT
tggcccagccagggtcaccctccccccagTGACGGAGCTGGCTGCTACACAGCCCGGGTGCACG
gagccaggggtcaccctccccccagTGACGGAGCTGGCTGCTACACAGCCCGGGTGCACG
AGATGTTCCAGGTATTTGAAGATGTTCAGCGCTGTCACTTCAAGAGGCCCAGGAGCTAG
AGGACGCTCAGGCGGGTCTGGGACCATAGGCCGGTCTGGTGTCCGTGTGGAGGGCCCC
TGAAGATCCGAGgtaaggctgtaaggctgtccccctgtccctatgagtgaccccgcctgctgctgc
aggtgctgacctgctgccccagctcctctcattcccgctccctcactcaggggacctccat
gtgcttctggcccatcccagtccacccaggacggggaggctg ctggaccacaggctgctggtcaggaaccagctgcatgctgccaggatgggaatgaggg
cgtgcagccaggggcacgcagactcccagaatgcagagagggtgccaccactccctctc
caccccagccccgctgtgctgtctctgcagGCCAGGTGGATGTGGAACAGGGATCA

FIG. 7B

TCTGCGAGAACATCCCCATCGTCACGCCCTCAGGAGAGGTGGTGGCCAGCCTCAACA
TCAGGgtaggtccagcggggaggcgccagccacgcacatatgcaagcctcagcccttgg
cttcccgcctgtctgctgcaacagccattgtccctagatgtacgtggcaggtgggcc
aagtcaaggtgagagaccaacgtgtcctgactg tcccccaggccctgctgtccctatcaagagatcaagatggcctgcgtgtgctgcctcgg
gcattgggagcctctcaaggctggtcaggaggccataggtacggggaagggcctgcgct
ctctggcgtcagcggctgttgccctgcagGTGGAGGAAGGCATGCTCTGCTCATCACA
GGCCCAATGGCTGCGGCAAGAGCTCCCTGTTCCGGATCCTCGGGTGGGCTCTGCCCACG
TACGGTGTGTGCTCTACAAGCCCCCACCCAGCGCATGTTCTACATCCCGCAGAGgtaa
ggaagcccgtgcgccctctccaccctcttcctgcctgtgcgctcacacatgcttcctg
cagaggcccaggaagtggtgaagagtcagcacctcaggagagacactgcactgtcc
ccagagcagagacgggctgtgtttcctgctgttcctgtgcacgggcgatgtgagcgtgtgtga
gtttggatctgtgtggggtgtgtgcacgggcgatgtgagcgtgatgcgtgtgtga
gcgtggcatgtggacactgcctggaggcgcagagtatcttggggggaggcagagccggcc
cttccctccgtggacaccccagctttcccacagcCCCTACATGTCTGTGGGCTCCCTGCGT
GACCAGGTGATCTACCCGGACTCAGTGGAGGACATGCAAAGGAAGGGCTACTCGGAGCAG
GACCTGGAAGCCATCCTGGACGTCGTGCACCTGCACCACATCCTGCACCCTTGCCTTCCAG
aggaggcctggggctgcagccaccctttgtcccacccttgtcctctccttgcctccag
ggagtgaagattacctcaacatccagagtctaaagtgccaggtgccacggggcggggcag
aggctgctaccagggaggaccaacacca

FIG. 7C

```
atgattaatgcctgtcagacagacaaggacgcagaggcacagggccctgtcgtcacagc
tagctcattcccgcagctccccagctccccagctccccgggtctgggtgctggtgg
aactgagccaagaccattgcccccgcctagGTTGGGAGGCTATGTGTGACTGGAAGGACG
TCCTGTGGGTGCGAGAAGCAGAGAGAATCGGACCCGCATGTCTACCAGgtgag
cactccggaccggcaggctccctgggtccctggaagggaagtagcagctgtggggag
GCCTGGGCTCAGTGGAGCCTGAGCGTGTTGGGCCCTGAGGGTGCACAGAC
TCTCCTCTCGCCCGGACCCCAGGCCCAAGTACGCCCCTCTGGATGAATGCACCAGCGC
CGTGAGCATCGACGTGGAAGGCAAGATCTTCCAGGCGGGCAAGGACGCGGGCATTGCCCT
GCTCTCCATCACCCACCGGCCCCTCCCTGTGtaggtgccctgtctccctgggtcg
gtgggagtgcctgcctgaggggaggggtggccccgggccagcaggcggct
gtcatcagcagccccgtgccctgacccctgtccctctcctgccagGAAATACC
ACACACACTTGCTACAGTTCGATGGGAGGGAGAAGCAGCTGGAGCTGGACTCAG
CTGCCCGCCTGAGCCTGACGGGACAGGCCTGAGCAGCAGCCGCTGGCCGCGGCATTC
CCAAGATGCAGCCGGGCCACCGGCCTTCCAAGATCCTGGGCGAGGCCGTGGCCCAG
CGCATGTGCCGGCCACCTAGCCCTGGCCTTCCAGGTGCCTTCCACCTGAC
ACAACCGTCCCCGGCCCCCTGCCCCCCAAGCTCGATCACATGAAGAGACAGCAGC
ACCCACCACGCACGCACCCCCCTGGCCCATGCCCCCTCCTCCTAGAAAACCCTTC
CCGCC
```

FIG. 7D

X-LINKED ADRENOLEUKODYSTROPHY GENE AND CORRESPONDING PROTEIN

BACKGROUND OF THE INVENTION

The present application relates to the identification and isolation of a gene which is responsible for the adrenoleukodystrophy. It further concerns the protein encoded by this gene and their use in diagnostic or therapeutic procedures.

Adrenoleukodystrophy (ALD) is an X-linked disease affecting 1/20,000 males either as cerebral ALD in childhood or as adrenomyeloneuropathy (AMN) in adults. Childhood ALD is the more severe form, with onset of neurological symptoms between 5–12 years of age. Central nervous system demyelination progresses rapidly and death occurs within a few years. AMN is a milder form of the disease with onset at 15–30 years of age and a more progressive course. Adrenal insufficiency (Addison's disease) may remain the only clinical manifestation of ALD. The principal biochemical abnormality of ALD is the accumulation of very long chain fatty acids (VLCFA) because of impaired β-oxidation in peroxisomes. The normal oxidation of VLCFA-CoA in patients fibroblasts suggested that the gene coding for the VLCFA-CoA synthetase could be a candidate gene for ALD.

ALD or its variant ANN is a monogenic disease but its clinical expression can be under the control of several genes or factors, leading to phenotypic variability.

Adrenoleukodystrophy and adrenomyeloneuropathy are characterized by the presence of an abnormal ALD gene, resulting from deletions or other types of mutations including point mutations. The mututions in the gene may nevertheless remain clinically silent or may lead to various phenotypic clinical expression.

Although it well known that the gene responsible for the adrenoleukodystrophy is located on the Xq28 region of the X chromosome, the results which have been described up to now have not permitted to identify and characterize the gene responsible for the ALD.

Some experiments were for instance conducted in order to check any possible relationship between the alteration of the gene responsible for the colour vision and the ALD gene. The inventors have now shown that although these genes of the red/green colour pigment also map to the Xq28 region, they are not linked either structurally or functionally to the ALD gene.

For the purpose of this description, it is mentioned that the expression "ALD gene" encompasses the gene involved in ALD and also in its adult variant AMN.

SUMMARY OF THE INVENTION

The invention accordingly relates to an isolated nucleotide sequence which is for instance selected among DNA, RNA, CDNA sequences, responsible for the adrenoleukodystrophy or the adrenomyeloneuropathy.

By the expression "sequences responsible for ALD or AMN" it must be understood that the abnormal form of the ALD gene is involved in the ALD pathology; of course the normal gene (devoid of mutations, especially of deletions) does not cause the disease.

The term "isolation" refers to the fact that the nucleotide sequence is separated from the other nucleotide sequences of the Xq28 region of the X chromosome when it is purified for instance from a natural source or organism. This isolated nucleotide sequence is also obtainable from synthetic or semi-synthetic sources, according to well-known methods. This sequence can be any type of nucleotide sequence and especially can be selected among DNA, RNA or cDNA.

A particular sequence which is referred to according to the invention consists essentially of the human gene responsible for the ALD. This gene accordingly contains both exons and introns and therefore contains both coding sequences of the gene and regulation sequences.

A preferred embodiment of the invention provides for an isolated nucleotide sequence having the sequence represented on FIG. 6 (SEQ ID NO:4–17) and FIG. 7 (SEQ ID NO:8–23).

The inventors have shown that the gene coding for the ALD protein, contains 10 exons and 9 introns. It must be noted that the deletions and/or mutations which affect the gene and which accordingly are capable of giving rise to the ALD disease or its variant AMN, can be situated either in the exons or in the introns. When these modifications affect the intron sequences, they are often located in the sequence of the intron which is adjacent to the coding sequence. Presence of a mutation in the gene is a condition necessary for the expression of the disease but can remain insufficient to lead to the expression of clinical symptoms related to this disease.

According to another preferred embodiment of the invention, the nucleotide sequence consists of the coding sequence of the gene.

In particular, this coding sequence can be a cDNA corresponding to the sequence represented on FIG. 2 (SEQ ID NO:1).

According to another embodiment of the invention, the isolated DNA sequence is characterized in that it consists essentially of a DNA sequence encoding the human adrenoleukodystrophy protein. In such a case, the DNA sequence codes for the amino-acid sequence represented on FIG. 2 (SEQ ID NO:2).

The invention further rebates to nucleotide sequences which are modified regarding the above described sequence but which nevertheless hybridize under stringent conditions defined hereafter with a nucleotide sequence as described above. Such a sequence contains preferably at least 10 nucleotides and has advantageously a length of around 20 to 100, preferably 20 to 50 nucleotides.

A preferred nucleotide sequence of the invention can further be characterized by the restriction map which is given on FIG. 5 or by the structural organization which is also given on FIG. 5.

The invention also concerns nucleotide fragments selected among DNA or cDNA fragments, which contain at least 10 nucleotides and advantageously at least 20 nucleotides, and are capable of hybridizing specifically, with a sequence which has been defined hereabove.

The hybridization is said specific if the nucleotide fragment does not hybridize for instance with the DNA sequence of the human PMP protein or the DNA of other proteins of the ATP binding protein superfamily.

The fragments of the invention can be labelled in order for instance to be used as probes or can be also involved as primers for amplification reactions and especially for PCR reactions.

The probes of the invention are advantageously labelled by any label classically used. They may be labelled with the aid of a radioactive marker such as $^{32}P$, $^{35}S$, $^{125}I$, $^{3}H$, $^{14}C$ and the radioactive labelling may be performed by any method known to the person skilled in the art.

The probes may be label led at the 3' end by addition of one or more deoxynucleotides or ribonucleotides or by a dideoxynucleotide labelled in the alpha position by means of $^{32}$P, in the presence of the terminal deoxynucleotidyl transferase, or at the 5' end by transfer of a radioactive phosphate group of a free deoxynucleotide or dideoxynucleotide labelled in the gamma position in the presence of the T4 DNA ligase. The probes may also be labelled by using a DNA polymerase by means of "nick translation" or "random priming" or "polymerase chain reaction".

The method of detection of the hybridization will depend on the radioactive label used and may be based on autoradiography, liquid scintillation, gamma counting or any other technique making possible the detection of the radiation emitted by the radioactive label.

Non-radioactive labelling may also be used by combining with probes groups exhibiting immunological properties such as an antigen, a specific affinity for certain reagents such as a ligand, physical properties such as fluorescence or luminescence, properties making possible the completion of enzymatic reactions such as an enzyme or an enzyme substrate. The non-radioactive labelling may also be performed directly by chemical modification of the DNA, such as photobiotinylation or sulfonation.

A particular fragment which can be used as a probe is the fragment which is designated by "X2" and which corresponds to an XbaI-EcoRI fragment of 1.8 kb included in the sequence represented on FIG. 6.

Other preferred probes are those designated by Ex13 and Ex3 and represented on FIG. 2.

Particularly preferred fragments to be used as primers for amplification procedures are those which are situated within the sensitive parts of the gene, i.e., the parts which may be more susceptible to mutations or deletions, or also fragments which are surrounding these regions.

Interesting primers are for instance those corresponding to sequences extending from position 1,853 to position 1,872 or from position 1,854 to position, 1,874 or from position 2,357 to position 2,375 as shown on FIG. 2 (SEQ ID NO:1).

The diagnosis can be made to detect the anomaly of the gene in patients presenting clinical symptoms of the disease or unaffected persons capable of transmitting the disease, especially in women carriers or as a neonatal screening.

The invention at so concerns a pharmaceutical composition comprising an isolated nucleotide sequence according to the definitions given above, together with a physiological acceptable pharmaceutical vehicle.

A particularly useful pharmaceutical composition is one which contains the genomic DNA of the ALD gene or the cDNA corresponding thereto.

Another aspect of the invention relates to a protein consisting essentially of the adrenoleukodystrophy protein.

In a preferred embodiment, this protein characterized by the amino-acid sequence given in FIG. 2 (SEQ ID NO:2).

The invention also relates to a protein having a sufficient homology with the amino-acid sequence given above, to have the essential biological properties the ALD protein.

These biological properties are the ability to complement the biological defect in cells from patients with ALD or AMN, or to share immunological determinants (epitopes) with the ALD protein.

Another protein within the scope of the invention has the essential biological properties described above and is such that the 52 amino-acid residues of its C-terminal end have an homology or at least 75%, preferably 80% and more preferably 90% with the aligned amino-acid sequence which has been given above.

The invention also relates to amino-acid fragments or sequences containing at least 7 amine-acid residues, which fragments are recognized by antibodies that bind specifically the protean of the invention.

Preferred fragments contain from 7 to around 745 or 500 amino-acids, advantageously from 7 to around 100, preferably from 7 to around 50 and most preferably from 7 to around 20.

Particular amino-acid sequences are derived from regions of the sequence represented on FIG. 2, which are specific for the ALD protein and especially which are not common to sequences of human and rat 70KPMP protein and other members of the ATP binding protein superfamily, such as those described in the publication of Mosser J. et al (Nature, vol. 361, 25 Feb. 1993, pages 736–730).

The antibodies capable of binding preferably specifically the ALD protein of the invention, especially monoclonal antibodies are obtained according to usual methods, involving the production of hybridoma cells, formed by fusion of spleen cells of an animal previously immunized with a protein of the invention and myeloma cells.

Specific monoclonal antibodies detect a protein having an apparent molecular weight of 75 kDa.

The invention further encompasses the antibodies, either monoclonal or polyclonal that bind specifically the protein according to the above definition.

The specific binding can be checked by assaying these antibodies with proteins having homologies with the ALD protein, for instance with the rat or human 70 peroxisomal membrane protein (PMP) or other proteins of the ATP binding protein superfamily as cited above. The antibodies of the invention are those which do not bind these different proteins presenting some homology with the ALD protein.

The nucleotide sequence or protein or fragments thereof of the invention are useful for diagnostic or therapeutic purposes.

Especially the nucleotide sequences or fragments as defined above can be used in a process for the in vitro diagnosis of the ALD or AMN disease in a human patient, these sequences being used as probes or as primers.

Usual techniques like those which are involved in the detection of genetic diseases are for instance southern blotting RFLP (Restriction Fragment Length, Polymorphism) detection or PCR reactions.

The detection of the protein can be performed using specific antibodies, monoclonal or polyclonal.

The detection is performed on samples containing for instance blood cells.

In the present case due to the possibility of various mutations of the ALD gene, it can be useful to have recourse to multiplex PCR, using different primers for amplification of several regions of the gene.

The invention also relates to a process for the treatment of cells and especially somatic cells of a human patient affected by ALD or AMN, comprising the administration to the patient of cells previously modified with a nucleotide sequence as described above. The cells can be modified by recombinant nucleotide sequences containing one of the DNA, cDNA or RNA sequence of the invention, under the control of regulation elements in a vector appropriate for the modification or transfection of cells. Advantageously the regulation elements are capable of ensuring a high level of expression and comprise accordingly strong promoters, possibly an enhancer and in some instances a reporter gene such as for example the neo gene or the dhfr gene.

Appropriate vectors can be plasmid vectors, retroviruses vectors or for instance adenoviruses vectors.

The transfer of the sequence useful for therapeutic purposes is performed by ex vivo techniques like electroporation, transfection especially calcium phosphase transfection or fusion for instance with liposomes.

The somatic transfer can also be performed in vivo using cells as vectors, which cells are previously modified ex vivo with the gene of interest. Accordingly hematopoietic cells or nervous cells are used. Among the techniques which are available for in vivo transfer of gene one can further cite inert vectors like liposomes, viral vectors, especially retroviruses or adenoviruses or directly by injection of DNA.

The vectors used for the somatic transfer of the gene or sequences of the invention can also be directly transfered in vivo, for instance by direct injection in the blood stream or by stereotactic injection in specific regions of the brain (Strattford-Perricaudet LD et al J Clin Invest 90, 626–630. Akli Set al Nature genomics vol 3, March 1993).

The direct administration of DNA has been described for instance by Wolff J. A. et al (1990, Science 247, 1465–1468) or Acsadi G. et al (1991, Nature 352, 815–818).

As example, for the preparation, of the vector, the sequence of the ALD gene, preferably the cDNA corresponding to the ALD gene is inserted in a defective murine Moloney vector (Mo-MLV), under the control of regulation elements. The defective vector still contains its cis-sequences such as the LTR sequence or part thereof sufficient for the transcription and integration, the psi sequence necessary for the encapsidation and the PB sequence for viral replication. In this vector the vital genes gag, pol, env are at least partly deleted and substituted with the sequence of interest. This sequence is placed under the control of its own promoter or a stronger promoter such as the SV40 promoter. A marker gene is possibly added to the construction.

The helper virus used contains the retroviral genes (gag, pol, env) necessary for replication of the vital genome and for the formation of the vital particles. To the contrary the cis-sequences which are present in the vector are deleted in the helper virus.

The helper provirus is inserted in a murine cell line especially NIH/3T3 as host.

The vector is then transfected in the cell line allowing the production of viral particles.

From a general point of view, the techniques used for the transfer of the human ADA gene (Adenosine denaminase) in cells can be also used in the present situation. Like the ADA gene, the ALD gene or its cDNA is transfected with a retrovirus in fibroblast cells (Palmer et al. PNAS, 1987, 84, 1055–1059), or in lymphocytes or other hematopoietic cells including proursor or stem cells (Culver et al. Hum Gene Ther 2,107 1991 or Anderson WF Science vol 256 May 6 1992 p808)

Other characteristics and advantages of the invention will become apparent from the examples add figures.

BRIEF DESCRIPTION OF THE DRAWINGS

FIG 1a–1e Map of the ALD gene region and its rearrangements in patients a, Chromosomal rearrangement in patient O. The joining of BP4-BP2 and BP3-BP1 were demonstrated by cloning the corresponding junction fragments (dashed lines). The extends of the two deletions (19.2 and 88 kb respectively) are indicated in b. Probe X2 (circle) is discussed in the examples and other probes (filled circles, Fr probes) are from Martinez, C. M. et al, (Cell Biol. int. Rep. 14, 255–266, 1990). The distance between probes Fr14 and Fr11 (broken line) is not known. The green cone pigment gene (GCP) is indicated by a box (G) . b, Map of the R/GCP genes and of the second deletion in patient O, including the rare cutter restriction sites (vertical bars, top) EagI (Ea), BssHII (Bs) , SacI (S), ClaI (C), NotI (N) and MluI (M). The rare cutter sites within the pigment gene-repeat unit are not marked. The extents of the two deletions (wavy lines) and the position of the 4 BPs in patient O are indicated. Probe Fr15.4 (deleted in patient O) was used to screen a Xq28-specific cosmid library, yielding 3 overlapping clones (cos Qc 11H12, cos Qc 8F3 and cos Qc 14A11). The red cone pigment (RCP) gene is indicated by the filed box (R) and the GCP bene by a box (G. c, Deletions detected in 5 ALD patients and restriction map of the subcloned region of ALD gene using the following enzymes: EcoRl (E), HindIII (H), BamHI (B), and XbaI (X). Rare cutter sites are indicated as in b. Localization or subcloned probes is shown at the top. Probe X2 (box) is a 1.8 kb XbaI-EcoRI restriction fragment derived from X-8, the second junction fragment (BP4-BP2) in patient O. TA25 (2.1 kb), Ta4 (3.6 kb), Ta1 (1.0 kb), Ta18 (0.85 kb), Ta13a (935 bp) and Ta13b (252 bp) are TaqI-digested DNA fragments (hatched boxes) derived from subcloning of cosmid Qc 11H12. d, Segregation of an abnormal junction fragment detected by probe X2 in ALD family B. Probe X2 hybridizes to a 16-kb HindIII fragment in normal individuals (open square and circle). An abnormal 14.4-kb junction fragment was detected in an affected ALD patient (pat lent B; see panel c) and in all heterozygous females. e, Detection of the same rearranged DNA fragment in two ALD brothers with different clinical ALD phenotypes by southern blot analysis of HindIII-digested DNA from 3 brothers (Family Ma; sec c) hybridized with probe X2. An abnormal junction, fragment of 22kb is detected by X2 in a male with cerebral ALD (filled square) and his brother with Addison's disease (hatched square).
METHODS. Restriction patterns of the cosmids were analysed as described. Cosmid Qc 11H12 was digested with TaqI and cloned directly in the ClaI site of pBluescript SK$^+$ (Stratagene). X-8 was isolated from a XbaI genomic library constructed in bacteriophage (Stratagene) using DNA from a somatic hybrid line containing the X chromosome of patient O. Gel electrophoresis, southern blotting, probing and autoradiography were all done as described.

FIGS. 2A–2B: Sequence of ALD-protein cDNA (SEQ ID NOS:1 and 2). The sequence is derived from analysis of clones obtained by exon connection and clones isolated from a HcLa cDNA library, and confirmed in most cases by sequences of genomic clones.

METHODS. Four probes (Ta25, Ta1, Ta18 and TA13b) derived from subcloning of cosmid Qc 11H12 were sequenced. Candidate exons, strand and frame assignments were screened by the GRAIL program (Oak Ridge, RN). Oligonucleotide primers were designed according to the coding regions that presented highest homology score to 70K PMP in TA25, TA18, and TA13b. Ex13 and Ex3 are cDNA clones obtained by exon connection in 2-step-boosted or nested polymerase reactions (30 cycles with external primers and 40 cycles with internal primers) performed on oligo(dT)-primed cDNA Total RNA (20 µg) from a lymphoblastoid cell line was used as starting material. External primers correspond to positions 1,853–1,872 (for Ex13), and to positions 1,854–1,874 and 2,357–2,375 (for Ex3). Internal primers are indicated by arrows. Subsequent amplification products were blunt-ended by action or T4 DNA polymerase (New England Biolabs), directly cloned in pBluescript KS$^+$ vector (Stratagene), sequenced using dideoxynucleotide termination (applied Biosystems), and analysed on an automated DNA sequencer (Applied Biosystems).

Figures 3A, 3B:
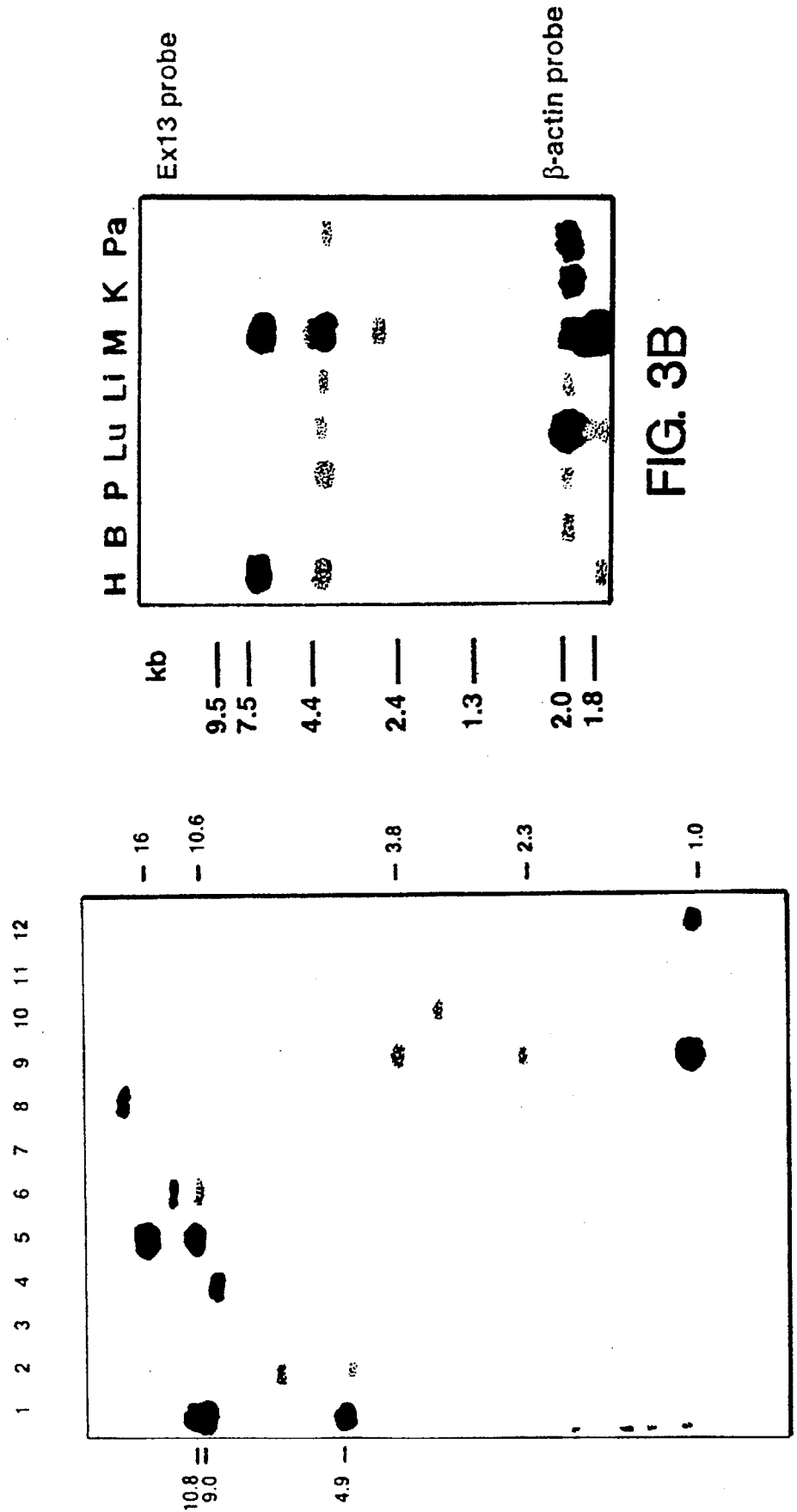

FIGS. 3a–3b, Detection of deletions in the DNA isolated from three ALD patients using cDNA probe Ex13. DNA was digested with EcoRI (lates 1–4), HindIII (lanes 5–8) and TaqI (lanes 9–12). Lanes 1, 5 and 9: normal woman; lanes 2, 6 and 10: patient L; lanes 3, 7 and 11: patient R; lanes 4, 8 and 12: patient Ma. The 10.8-kb EcoRI normal fragment (lanes 2–4) and the 12.5 -kb HindIII abnormal junction fragment from patient R (lane 7) hybridize to only around 60 bp of the Ex13 probe and are thus very fait. Sizen (in kb) of normal restriction fragments are indicated on the left and on the right. Similar results were obtained with Ex3 in ALD patients deleted in 3' end region of the ALD gene. b, Northern blot analysis with probe ex13. cDNA Ex13 hybridized to northern blot (top) of human poly (A)$^+$ RNA detects a transcript of 4.2 kb which is expressed in heart (H), placenta (P), lung (Lu), liver (Li) skeletal muscle (M), pancreas (Pa) and, to a lesser extent, in brain (B) and kidney (K). Two other transcripts are detected in heart and skeletal muscle (6.8 kb) and in liver and skeletal muscle (2.75 kb). RNA size markers are indicated on the left. A human, β-actin probe hybridized to the same northern blot (bottom panel) detects two transcripts of 2.0 and 1.8 kb, respectively. METHODS. Gel electrophoresis, southern blotting, probing and autoradiography were done as described. For b, human multiple-tissue northern blot was purchased from Clontech. Membranes were exposed at −70° C. to X-ray film for 5d (Ex13 or EX3 probes) or for 6 h (β-actin probe).

Figure 5:
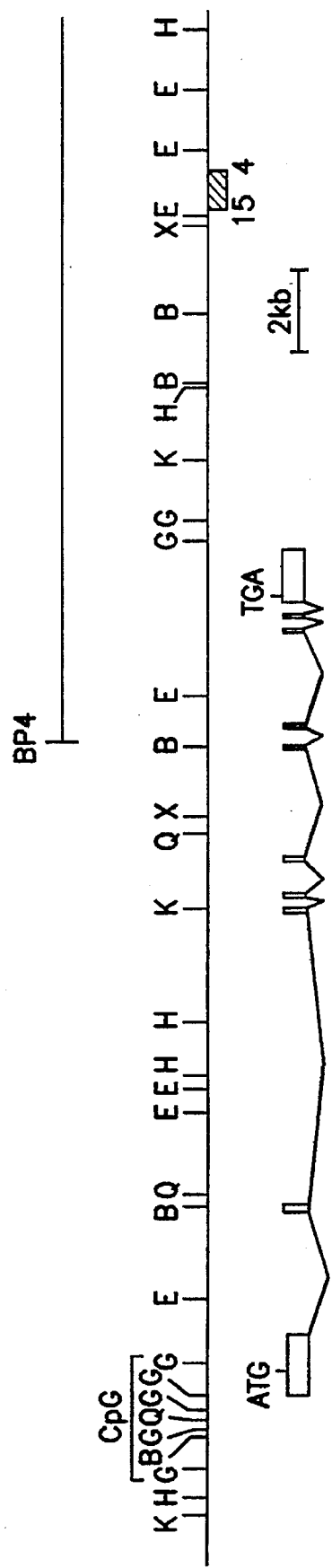

FIGS. 4A–4B. Sequence alignment of ALD protein (SEQ ID NO:2) and human 70K PMP (SEQ ID NO:3). Amino acid identities are indicated by two dots and conservative changes by one. Sequence similarities were established with the FASTP program. FIG. 5. Structural organization of the ALD gene The distribution of the 10 ALD exons is shown with black boxes. Traduction initiation and termination sites (respectively in exon 1 and 10) are indicated. The location of the CpG island, the genomic probe FR15.4 (grey box) and the most centrometric breakpoint of patient O rearrangement (BP4) are also represented. FIG. 6. Intron-exon boundaries of the ALD gene (SEQ ID NO.4–17). First and last two bases of each exon are indicated in bold. The position (number between brackets) correspond to the published cDNA sequence (Mosser et al, Nature). The average size of the gap within the sequence is specified for large introns. Sequence of small introns is fully represented.

FIGS. 7A–7D Complete DNA sequence of the ALD gene (SEQ ID NO:18–23). It contains both the cDNA sequence (in capital letters) and the intron sequence (in small letters).

DETAILED DESCRIPTION OF THE INVENTION

EXAMPLES

I) Isolation and identification of the ALD gene

Here a positional cloning was used to identify a gene partially deleted in 6 of 85 independent patients with ALD. In familial cases, the deletions segregated with the disease. An identical deletion was detected in two brothers presenting with different clinical ALD phenotypes. Candidate exons were identified by computer analysis of genomic sequences and used to isolate complementary DNAs by exert connection and screening of cDNA libraries. The deduced protein sequence shows significant sequence identity to a peroxisomal membrane protein or $M_r$ 70K that is involved in peroxisome biogenesis and belongs to the "ATP-binding cassette" superfamily of transporters.

As previous attempts to purify VLCF-CoA synthetase were unsuccessful, a "positional cloning" approach was used.

Figures 1A, 1B, 1C:
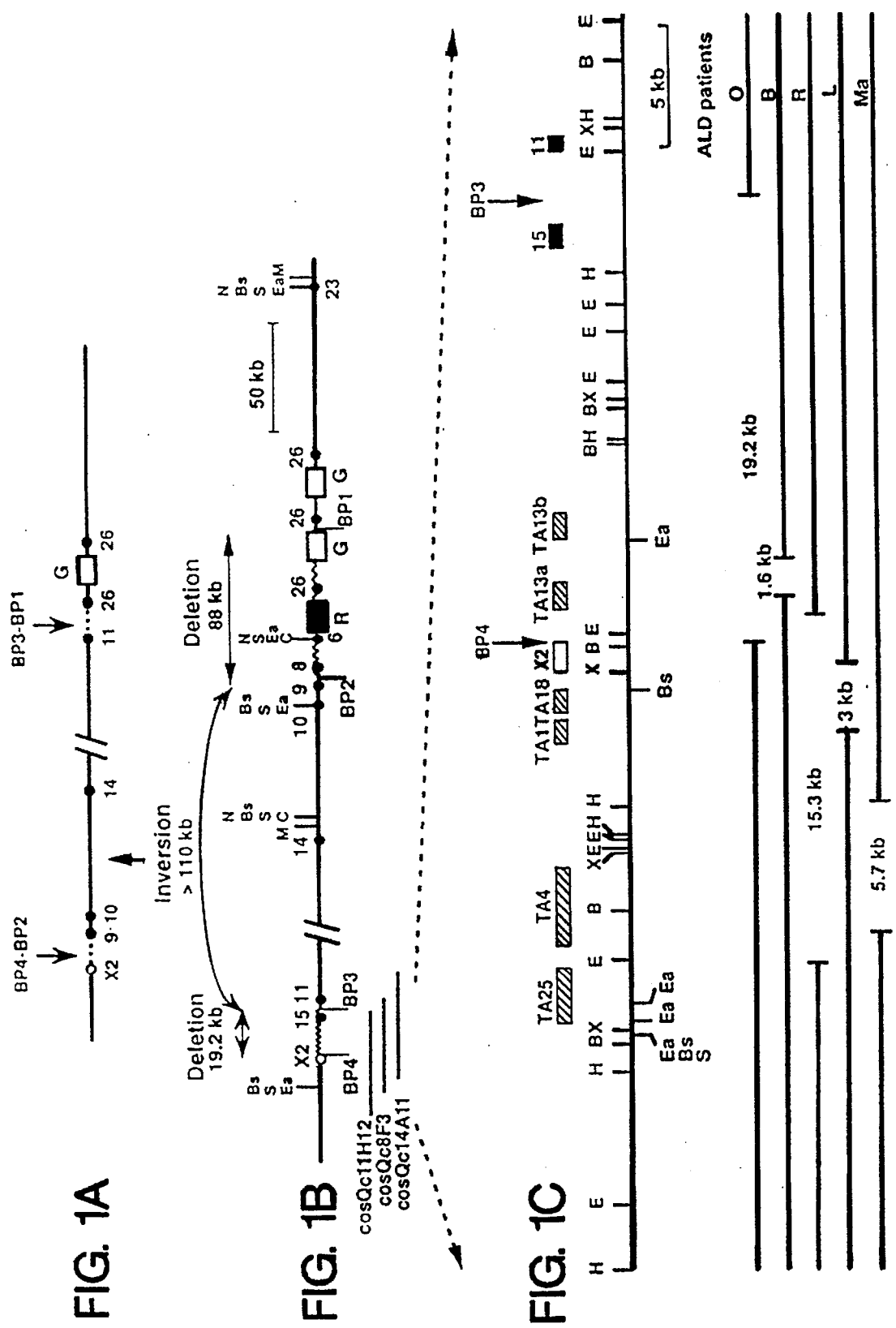

The ALD locus has been mapped to Xq28 (deDuve, C. et al, Biochem. Pharmac. 23, 2495–2531, 1974), where the red/green colour pigment (R/GCP) genes reside. On the basis of the high incidence (40%) of colour vision anomalies in AMN patients and earlier results, it was firstly proposed that ALD and R/GCP genes could be close together. Recently, an AMN patient with blue-monochromatic colour vision was identified who had a complex rearrangement located 5' of the red-colour pigment (RCP) gene, which included two deletions separated by a large (>110 kb) inversion (FIG. 1a and b). Only the RCP gene was found in the first deletion (88 kb). No additional deletion was detected in this region in 81 other ALD patients. It was then postulated that the inverted segment or the second deletion were candidate loci for the ALD gene.

Probes cot-responding to three of the breakpoints (BP) of this rearrangement were isolated (BP1, BP2 and BP3) (FIG. 1). To estimate the size of the second deletion a probe 4 kb proximal to Fr15 was used (deleted in patient O; Martinez et al, Cell Biol. Int. Rep. 14,255–266 (1990) to obtain clones from a Xq28 cosmid library. Three overlapping clones were obtained that spanned about 90 kb and contained a cluster of rare restriction cutting sites (EagI, BssHII, SacII) indicating the presence of a CpG island (FIG. 1c). In parallel, an XbaI junction fragment (X-8) corresponding to breakpoints 4 and 2 in patient O was cloned (FIG. 1a). A restriction map of X-8 showed that a 1–8 kb XbaI-EcoRI (X2) fragment contains a 1.6-kb segment on the BP4 side and included within the Fr15 cosmid contig described above (FIG. 1b and c). Breakpoints 3 and 4 are separated by 19.2 kb, and delimit the second deletion in patient O.

To search for conserved sequences in other mammalian species and to detect additional deletions in other ALD patients, cosmid Qc 11H12 was subcloned (FIG. 1b, c). Probes TA25, TA1, TA18 and TA13B (FIG. 1c) showed cross-hybridization to various mammalian species. More important, X2, TA4, TA18 and Ta13a probes detected deletions in five other ALD patients. Probe X2 allowed the detection of a junction fragment segregating with the disease in family B (FIG. 1d). In another family (Ma), probe X2 detected an identical 22-kh HindIII junction fragment in two brothers with different clinical phenotypes of ALD (FIG. 1e). The size of deletions ranged from 1.6 kb (patient B) to 15.3 kb (patient R) with partial overlap (FIG. 1c). Six patients had deletions (including patient O) in a population of 85 independent ALD patients, but no deletions were found in a panel of 82 control males. These results indicate that the region contains at least part or the ALD gene.

Figure 2A:
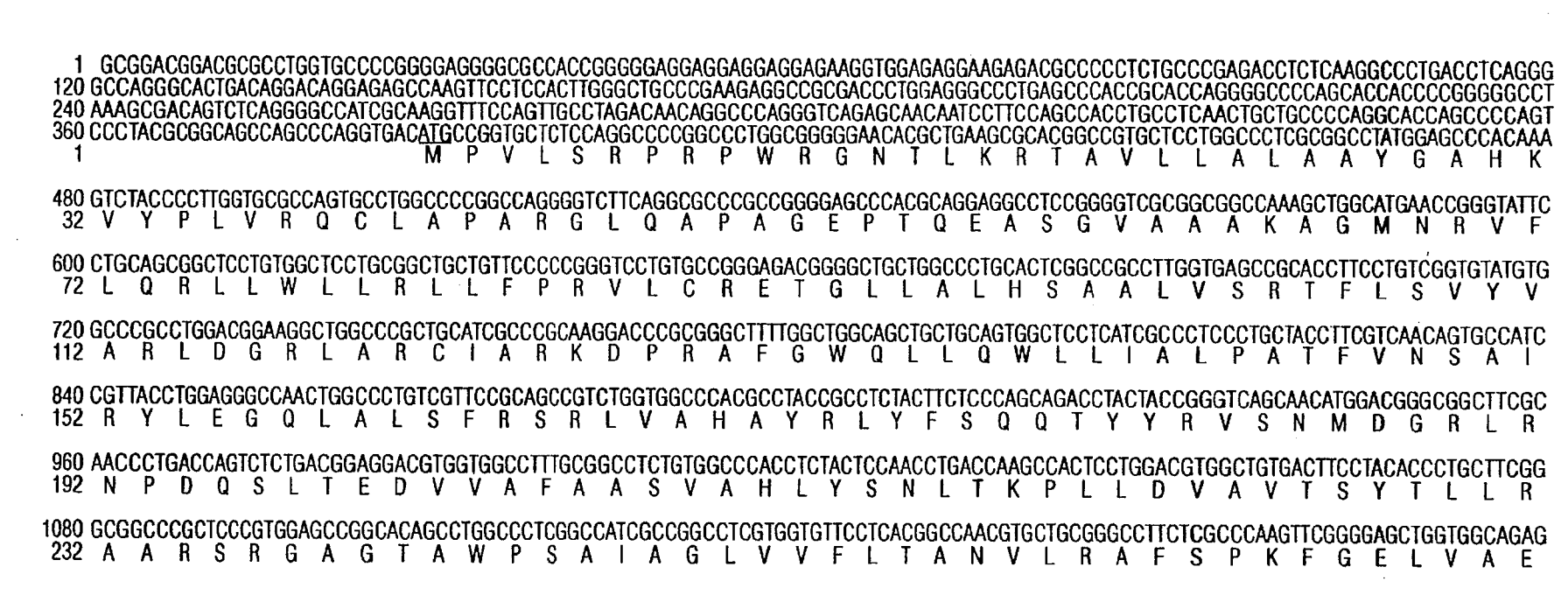
Figure 2B:
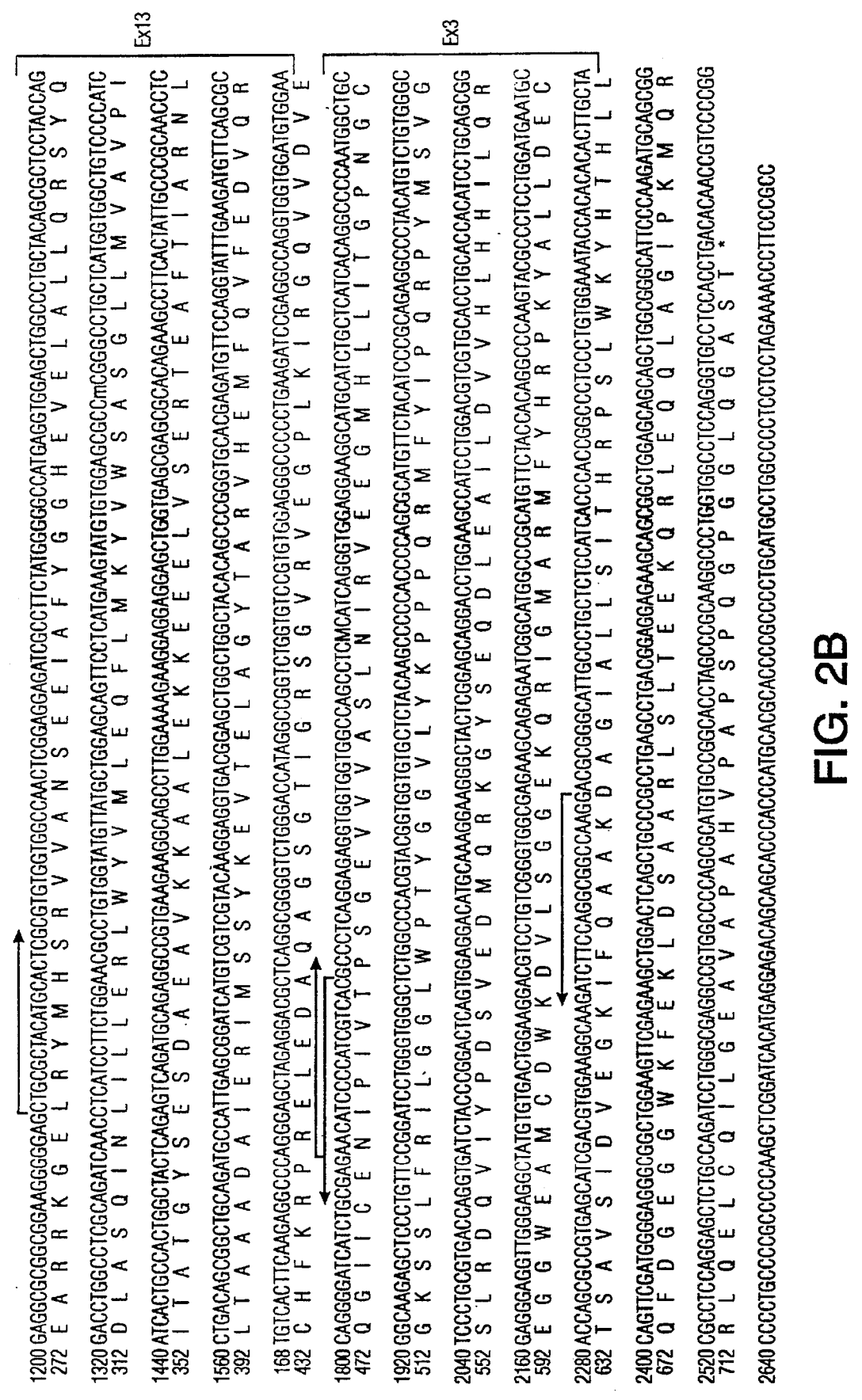

The sequences of probes Ta25, TA18, TA1.3b and of TA13a were determined and examined for putative coding regions (using a computer program based on a multiple sensor-neural netword approach) revealed a large (>700 bp) putative protein coding sequence within TA25 and smaller open reading frames (300–400 bp) in TA18, TA13 a and TA13b. The deduced amino-acid sequences showed significant sequence identity with collinearly positioned regions of human or rat 70K peroxisomal membrane protein (PMP). Nested-PCR reactions using primers from the putative exons (FIG. 2) produced two fragments (Ex13 and Ex3) of sizes (645 bp and 498 bp, respectively) compatible with those expected from homology with the 70K PMP cDNA. They hybridized to the predicted DNA fragments in normal individuals and to the same fragments detected by genomic probes in ALD patients (FIG. 3a). Ex13 and Ex3 have been used in combination to screen a random-primed HeLa cell cDNA library to obtain 6 independent overlapping clones.

The 2,751-bp sequence (FIG. 2) (SEQ ID NO:2) contains the whole protein-coding sequence of 745 amino acids (SEQ ID NO:2). The first methionine codon is preceded by an in-phase stop codon (at bp 282) and is included within a potential ribosome-binding sequence. Significant sequence identity with the 70K PMP (SEQ ID NO:3) begins at methionine 67 and ends at around 680 (corresponding to the carboxy terminus of 70K PMP). The remaining 52 amino acid residues are unique to the ALD protein (FIG. 4a).

The sequence of ALD protein (SEQ ID NO:2) could be aligned with human 70K PMP (SEQ ID NO:3) (Saari, J. C. & Bredberg, L. Biochim. biophys. Acta 716, 266–272, 1982)) with only a few deletions or insertions, and revealed a 38.5% amino-acid identity (253/659 amino acids) (FIG. 4a). When conservative amino acids substitutions are considered, the sequence similarity between the two protein sequences reached 78.9%. The two proteins show a similar hydrophobicity profiles, with a hydrophobic amino-terminal region containing potential transmembrane segments.

The hydrophilic carboxy-terminal region of the ALD protein shows 56% identity over 210 amino acids to the corresponding region of 70K PMP. The two characteristic nucleotide-binding consensus sequences are almost identical between the two proteins (underlined in FIG. 4b).

When northern blots of poly(A)$^+$ RNAs from human tissues were hybridized to probes Ex13 or EX3, a transcript of 4.2 kb was detected in heart, placenta, lung, liver, skeletal muscle, testis, pancreas and, to a lesser extent, in brain and kidney (FIG. 3b). The expression of the 4.2-kb transcript was very low in adult brain but more marked in 21-week fetal brain. A second transcript of 6.8 kb was detected in heart and skeletal muscle, whereas a third transcript of 2.75 kb was detected in muscle and liver. These additional transcripts could arise from alternative processing or the use of multiple polyadenylation sites. The sequence shown in FIG. 2 corresponds to 4.2-kb messenger RNA, this being the only species detected in HeLa cells.

The putative ALD gene has thus been identified in the distal part of Xq28 which has deletions in one or several exons in 6 of 85 independent ALD patients. Some of these deletions are small and non-overlapping, thus strengthening the conclusion that this gene is indeed involved in ALD. Although the gene coding for VLCFA-CoA synthetase was considered as a candidate gene for ALD, a recently cloned rat gene for long-chain ($C_{12}$–$C_{16}$) acyl-CoA synthetase failed to detect homologous sequences on the X chromosome. The putative ALD gene shows no homology to this latter sequence, or to the three other enzymes involved in peroxisomal β-oxidation. Surprisingly, a very significant sequence identity was found with human and rat 70K PMP. Two putative domains could be identified by hydropathy analysis: an amino-terminal hydrophobic region, which presumably contains six transmembrane segments, and a hydrophilic region containing ATP-binding motifs with striking identity to the ATP-binding region of the human 70K PMP. This sequence is well conserved in the ATP-binding cassette (ABC) family of transporters, which include the multidrug-resistant gene product, the cystic fibrosis transmembrane conductance regulator, and the products of the PSF1 and PSF2 genes, which encode peptide transporters and map in the class II region of the human MHC Complex (FIG. 4b). The conserved region includes the A and B consensus sequences (A; G-X4-G-K-T-X6-I/V; B: R/K-X3-G-X3-L(hydrophobic)4-D) of a nucleotide-binding fold, plus a 12-amino-acid motif highly conserved in ABC proteins (FIG. 4b).

ALD protein must therefore be a member of this superfamily of ABC transporters, which are also involved in transport of proteins, amino acids, inorganic ions and peptides in prokaryotes and eukaryotes. Although the predicted sequence of ALD protein (SEQ ID NO:2) shows significant identity to 70K PMP (SEQ ID NO:3), no homology was found to 35K PMP or to other PMPs required for peroxisome biogenesis in yeast. Although ALD was initially thought to involve a deficiency in peroxisomal VLCFA-CoA synthesase, the predicted sequence of the putative ALD protein rather suggests a protein involved in transport of VLCFA-CoA synthetase into the peroxisomal membrane or a protein that is functionally associated with the VLCFA-CoA synthetase in the peroxisomal membrane. The translocation of acyl-CoA oxidase, the next enzyme or the peroxisomal β-oxidation pathway, requires ATP hydrolysis, whereas the transport of VLCFA across the peroxisomal membrane does not, and neither is it impaired in peroxisomes from ALD patients.

Expression of ALD protein was observed in every tissue tested, but the relationship between ALD protein expression and the abundance of peroxisomes in tissues may not be straight-forward. Perosisomes are particularly abundant in liver and kidney, having an average diameter of 0.2–1 μM. In other tissues, including the brain and fibroblasts, they are less abundant and smaller (0.05–0.2 μM). This abundance and size difference may reflect a distinct membrane and matrix protein compositions of peroxisomes in different tissues. Although ALD is associated with a defective oxidation of VLCFA, this metabolic defect is mainly expressed in brain and adrenal tissues.

ALD is characterized by a striking variation in clinical phenotype. In family Ma, an identical deletion was found in two sibs, a boy who developed cerebral ALD at 8 years, and his brother who developed only very mild adrenal insufficiency at 13 years. Furthermore, deletions were associated with the adult form (patients O and R) as well as with the severe childhood form (patients B and L). These differences suggest that the phenotypic variability of ALD is probably due to secondary factors (possibly immunological) or to the influence of still unidentified modifier genes.

II) Transfer and expression of the cDNA sequence of the ALD gene 1) retroviral vector A defective murine Moloney vector (Mo-MLV) is used.

The defective vector still contains its cis-sequences such as the LTR sequence or part the thereof sufficient for the transcription and integration, the psi sequence necessary for the encapsidation and the PB sequence for Vital replication. In this vector the viral genes gag, pol, env are at least partly deleted.

The promoter of the ALD gene or advantageously a stronger promoter such as the PGK-1 promoter (phosphoglycerate kinase) or SV10 promoter replace the deleted vital gene.

The CDNA of the ALD gene is cloned within the defective vector, under the control of the promoter, in a chosen restriction site.

The retroviral vector is then introduced in a cell line for encapsidation, which cell line expresses the gag, pol and env vital genes. A cell line like NIH/3T3 previously modified with the helper virus (Danos et al, PNAS, 85, 6460–6465, 1988) is used.

The recombinant construct is introduced by transfection and the cells produce vital particles.

2) Infection of cells

The cells used for the transfer of the cDNA sequence are cultivated and contacted and incubated with the retroviral vector. The infected cells are then amplified sufficiently to be used for the treatment.

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 2750 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 387..2624

( x i ) SEQUENCE DESCRIPTION: SEQ ID NO:1:

```
GCGGACGGAC  GCGCCTGGTG  CCCCGGGGAG  GGGCGCCACC  GGGGGAGGAG  GAGGAGGAGA      60

AGGTGGAGAG  GAAGAGACGC  CCCCTCTGCC  CGAGACCTCT  CAAGGCCCTG  ACCTCAGGGG     120

CCAGGGCACT  GACAGGACAG  GAGAGCCAAG  TTCCTCCACT  TGGGCTGCCC  GAAGAGGCCG     180

CGACCCTGGA  GGGCCCTGAG  CCCACCGCAC  CAGGGCCCC   AGCACCACCC  CGGGGGCCTA     240

AAGCGACAGT  CTCAGGGGCC  ATCGCAAGGT  TTCCAGTTGC  CTAGACAACA  GGCCCAGGGT     300

CAGAGCAACA  ATCCTTCCAG  CCACCTGCCT  CAACTGCTGC  CCCAGGCACC  AGCCCCAGTC     360

CCTACGCGGC  AGCCAGCCCA  GGTGAC ATG  CCG GTG CTC TCC AGG CCC CGG CCC        413
                              Met Pro Val Leu Ser Arg Pro Arg Pro
                                1               5
```

| TGG CGG GGG AAC ACG CTG AAG CGC ACG GCC GTG CTC CTG GCC CTC GCG | 461 |
|---|---|
| Trp Arg Gly Asn Thr Leu Lys Arg Thr Ala Val Leu Leu Ala Leu Ala | |
| 10                15                  20                    25 | |

| GCC TAT GGA GCC CAC AAA GTC TAC CCC TTG GTG CGC CAG TGC CTG GCC | 509 |
|---|---|
| Ala Tyr Gly Ala His Lys Val Tyr Pro Leu Val Arg Gln Cys Leu Ala | |
|               30                  35                    40    | |

| CCG GCC AGG GGT CTT CAG GCG CCC GCC GGG GAG CCC ACG CAG GAG GCC | 557 |
|---|---|
| Pro Ala Arg Gly Leu Gln Ala Pro Ala Gly Glu Pro Thr Gln Glu Ala | |
|             45                  50                  55         | |

| TCC GGG GTC GCG GCG GCC AAA GCT GGC ATG AAC CGG GTA TTC CTG CAG | 605 |
|---|---|
| Ser Gly Val Ala Ala Ala Lys Ala Gly Met Asn Arg Val Phe Leu Gln | |
|           60                  65                  70           | |

| CGG CTC CTG TGG CTC CTG CGG CTG CTG TTC CCC CGG GTC CTG TGC CGG | 653 |
|---|---|
| Arg Leu Leu Trp Leu Leu Arg Leu Leu Phe Pro Arg Val Leu Cys Arg | |
|         75                  80                  85             | |

| GAG ACG GGG CTG CTG GCC CTG CAC TCG GCC GCC TTG GTG AGC CGC ACC | 701 |
|---|---|
| Glu Thr Gly Leu Leu Ala Leu His Ser Ala Ala Leu Val Ser Arg Thr | |
| 90                  95                  100                  105 | |

| TTC CTG TCG GTG TAT GTG GCC CGC CTG GAC GGA AGG CTG GCC CGC TGC | 749 |
|---|---|
| Phe Leu Ser Val Tyr Val Ala Arg Leu Asp Gly Arg Leu Ala Arg Cys | |
|                 110                  115                  120    | |

| ATC GCC CGC AAG GAC CCG CGG GCT TTT GGC TGG CAG CTG CTG CAG TGG | 797 |
|---|---|
| Ile Ala Arg Lys Asp Pro Arg Ala Phe Gly Trp Gln Leu Leu Gln Trp | |
|               125                  130                  135      | |

| CTC CTC ATC GCC CTC CCT GCT ACC TTC GTC AAC AGT GCC ATC CGT TAC | 845 |
|---|---|
| Leu Leu Ile Ala Leu Pro Ala Thr Phe Val Asn Ser Ala Ile Arg Tyr | |
|             140                  145                  150        | |

| CTG GAG GGC CAA CTG GCC CTG TCG TTC CGC AGC CGT CTG GTG GCC CAC | 893 |
|---|---|
| Leu Glu Gly Gln Leu Ala Leu Ser Phe Arg Ser Arg Leu Val Ala His | |
|           155                  160                  165          | |

```
GCC TAC CGC CTC TAC TTC TCC CAG CAG ACC TAC TAC CGG GTC AGC AAC          941
Ala Tyr Arg Leu Tyr Phe Ser Gln Gln Thr Tyr Tyr Arg Val Ser Asn
170             175             180             185

ATG GAC GGG CGG CTT CGC AAC CCT GAC CAG TCT CTG ACG GAG GAC GTG          989
Met Asp Gly Arg Leu Arg Asn Pro Asp Gln Ser Leu Thr Glu Asp Val
            190             195             200

GTG GCC TTT GCG GCC TCT GTG GCC CAC CTC TAC TCC AAC CTG ACC AAG         1037
Val Ala Phe Ala Ala Ser Val Ala His Leu Tyr Ser Asn Leu Thr Lys
        205             210             215

CCA CTC CTG GAC GTG GCT GTG ACT TCC TAC ACC CTG CTT CGG GCG GCC         1085
Pro Leu Leu Asp Val Ala Val Thr Ser Tyr Thr Leu Leu Arg Ala Ala
        220             225             230

CGC TCC CGT GGA GCC GGC ACA GCC TGG CCC TCG GCC ATC GCC GGC CTC         1133
Arg Ser Arg Gly Ala Gly Thr Ala Trp Pro Ser Ala Ile Ala Gly Leu
    235             240             245

GTG GTG TTC CTC ACG GCC AAC GTG CTG CGG GCC TTC TCG CCC AAG TTC         1181
Val Val Phe Leu Thr Ala Asn Val Leu Arg Ala Phe Ser Pro Lys Phe
250             255             260             265

GGG GAG CTG GTG GCA GAG GAG GCG CGG CGG AAG GGG GAG CTG CGC TAC         1229
Gly Glu Leu Val Ala Glu Glu Ala Arg Arg Lys Gly Glu Leu Arg Tyr
            270             275             280

ATG CAC TCG CGT GTG GTG GCC AAC TCG GAG GAG ATC GCC TTC TAT GGG         1277
Met His Ser Arg Val Val Ala Asn Ser Glu Glu Ile Ala Phe Tyr Gly
        285             290             295

GGC CAT GAG GTG GAG CTG GCC CTG CTA CAG CGC TCC TAC CAG GAC CTG         1325
Gly His Glu Val Glu Leu Ala Leu Leu Gln Arg Ser Tyr Gln Asp Leu
        300             305             310

GCC TCG CAG ATC AAC CTC ATC CTT CTG GAA CGC CTG TGG TAT GTT ATG         1373
Ala Ser Gln Ile Asn Leu Ile Leu Leu Glu Arg Leu Trp Tyr Val Met
    315             320             325

CTG GAG CAG TTC CTC ATG AAG TAT GTG TGG AGC GCC TCG GGC CTG CTC         1421
Leu Glu Gln Phe Leu Met Lys Tyr Val Trp Ser Ala Ser Gly Leu Leu
330             335             340             345

ATG GTG GCT GTC CCC ATC ATC ACT GCC ACT GGC TAC TCA GAG TCA GAT         1469
Met Val Ala Val Pro Ile Ile Thr Ala Thr Gly Tyr Ser Glu Ser Asp
            350             355             360

GCA GAG GCC GTG AAG AAG GCA GCC TTG GAA AAG AAG GAG GAG GAG CTG         1517
Ala Glu Ala Val Lys Lys Ala Ala Leu Glu Lys Lys Glu Glu Glu Leu
        365             370             375

GTG AGC GAG CGC ACA GAA GCC TTC ACT ATT GCC CGC AAC CTC CTG ACA         1565
Val Ser Glu Arg Thr Glu Ala Phe Thr Ile Ala Arg Asn Leu Leu Thr
        380             385             390

GCG GCT GCA GAT GCC ATT GAG CGG ATC ATG TCG TCG TAC AAG GAG GTG         1613
Ala Ala Ala Asp Ala Ile Glu Arg Ile Met Ser Ser Tyr Lys Glu Val
    395             400             405

ACG GAG CTG GCT GGC TAC ACA GCC CGG GTG CAC GAG ATG TTC CAG GTA         1661
Thr Glu Leu Ala Gly Tyr Thr Ala Arg Val His Glu Met Phe Gln Val
410             415             420             425

TTT GAA GAT GTT CAG CGC TGT CAC TTC AAG AGG CCC AGG GAG CTA GAG         1709
Phe Glu Asp Val Gln Arg Cys His Phe Lys Arg Pro Arg Glu Leu Glu
            430             435             440

GAC GCT CAG GCG GGG TCT GGG ACC ATA GGC CGG TCT GGT GTC CGT GTG         1757
Asp Ala Gln Ala Gly Ser Gly Thr Ile Gly Arg Ser Gly Val Arg Val
        445             450             455

GAG GGC CCC CTG AAG ATC CGA GGC CAG GTG GTG GAT GTG GAA CAG GGG         1805
Glu Gly Pro Leu Lys Ile Arg Gly Gln Val Val Asp Val Glu Gln Gly
        460             465             470

ATC ATC TGC GAG AAC ATC CCC ATC GTC ACG CCC TCA GGA GAG GTG GTG         1853
Ile Ile Cys Glu Asn Ile Pro Ile Val Thr Pro Ser Gly Glu Val Val
    475             480             485
```

```
GTG GCC AGC CTC AAC ATC AGG GTG GAG GAA GGC ATG CAT CTG CTC ATC        1901
Val Ala Ser Leu Asn Ile Arg Val Glu Glu Gly Met His Leu Leu Ile
490             495                 500                     505

ACA GGC CCC AAT GGC TGC GGC AAG AGC TCC CTG TTC CGG ATC CTG GGT        1949
Thr Gly Pro Asn Gly Cys Gly Lys Ser Ser Leu Phe Arg Ile Leu Gly
                510                 515                 520

GGG CTC TGG CCC ACG TAC GGT GGT GTG CTC TAC AAG CCC CCA CCC CAG        1997
Gly Leu Trp Pro Thr Tyr Gly Gly Val Leu Tyr Lys Pro Pro Pro Gln
            525                 530                 535

CGC ATG TTC TAC ATC CCG CAG AGG CCC TAC ATG TCT GTG GGC TCC CTG        2045
Arg Met Phe Tyr Ile Pro Gln Arg Pro Tyr Met Ser Val Gly Ser Leu
        540                 545                 550

CGT GAC CAG GTG ATC TAC CCG GAC TCA GTG GAG GAC ATG CAA AGG AAG        2093
Arg Asp Gln Val Ile Tyr Pro Asp Ser Val Glu Asp Met Gln Arg Lys
    555                 560                 565

GGC TAC TCG GAG CAG GAC CTG GAA GCC ATC CTG GAC GTC GTG CAC CTG        2141
Gly Tyr Ser Glu Gln Asp Leu Glu Ala Ile Leu Asp Val Val His Leu
570                 575                 580                 585

CAC CAC ATC CTG CAG CGG GAG GGA GGT TGG GAG GCT ATG TGT GAC TGG        2189
His His Ile Leu Gln Arg Glu Gly Gly Trp Glu Ala Met Cys Asp Trp
                590                 595                 600

AAG GAC GTC CTG TCG GGT GGC GAG AAG CAG AGA ATC GGC ATG GCC CGC        2237
Lys Asp Val Leu Ser Gly Gly Glu Lys Gln Arg Ile Gly Met Ala Arg
            605                 610                 615

ATG TTC TAC CAC AGG CCC AAG TAC GCC CTC CTG GAT GAA TGC ACC AGC        2285
Met Phe Tyr His Arg Pro Lys Tyr Ala Leu Leu Asp Glu Cys Thr Ser
        620                 625                 630

GCC GTG AGC ATC GAC GTG GAA GGC AAG ATC TTC CAG GCG GCC AAG GAC        2333
Ala Val Ser Ile Asp Val Glu Gly Lys Ile Phe Gln Ala Ala Lys Asp
    635                 640                 645

GCG GGC ATT GCC CTG CTC TCC ATC ACC CAC CGG CCC TCC CTG TGG AAA        2381
Ala Gly Ile Ala Leu Leu Ser Ile Thr His Arg Pro Ser Leu Trp Lys
650                 655                 660                 665

TAC CAC ACA CAC TTG CTA CAG TTC GAT GGG GAG GGC GGC TGG AAG TTC        2429
Tyr His Thr His Leu Leu Gln Phe Asp Gly Glu Gly Gly Trp Lys Phe
                670                 675                 680

GAG AAG CTG GAC TCA GCT GCC CGC CTG AGC CTG ACG GAG GAG AAG CAG        2477
Glu Lys Leu Asp Ser Ala Ala Arg Leu Ser Leu Thr Glu Glu Lys Gln
            685                 690                 695

CGG CTG GAG CAG CAG CTG GCG GGC ATT CCC AAG ATG CAG CGG CGC CTC        2525
Arg Leu Glu Gln Gln Leu Ala Gly Ile Pro Lys Met Gln Arg Arg Leu
        700                 705                 710

CAG GAG CTC TGC CAG ATC CTG GGC GAG GCC GTG GCC CCA GCG CAT GTG        2573
Gln Glu Leu Cys Gln Ile Leu Gly Glu Ala Val Ala Pro Ala His Val
    715                 720                 725

CCG GCA CCT AGC CCG CAA GGC CCT GGT GGC CTC CAG GGT GCC TCC ACC        2621
Pro Ala Pro Ser Pro Gln Gly Pro Gly Gly Leu Gln Gly Ala Ser Thr
730                 735                 740                 745

TGACACAACC GTCCCCGGCC CCTGCCCCGC CCCCAAGCTC GGATCACATG AAGGAGACAG      2681

CAGCACCCAC CCATGCACGC ACCCCGCCCC TGCATGCCTG GCCCTCCTC CTAGAAAACC      2741

CTTCCCGCC                                                             2750
```

( 2 ) INFORMATION FOR SEQ ID NO:2:

( i ) SEQUENCE CHARACTERISTICS:
        ( A ) LENGTH: 745 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Pro | Val | Leu | Ser | Arg | Pro | Arg | Pro | Trp | Arg | Gly | Asn | Thr | Leu | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Thr | Ala | Val | Leu | Leu | Ala | Leu | Ala | Ala | Tyr | Gly | Ala | His | Lys | Val |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Pro | Leu | Val | Arg | Gln | Cys | Leu | Ala | Pro | Ala | Arg | Gly | Leu | Gln | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Pro | Ala | Gly | Glu | Pro | Thr | Gln | Glu | Ala | Ser | Gly | Val | Ala | Ala | Ala | Lys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ala | Gly | Met | Asn | Arg | Val | Phe | Leu | Gln | Arg | Leu | Leu | Trp | Leu | Leu | Arg |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Leu | Leu | Phe | Pro | Arg | Val | Leu | Cys | Arg | Glu | Thr | Gly | Leu | Leu | Ala | Leu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| His | Ser | Ala | Ala | Leu | Val | Ser | Arg | Thr | Phe | Leu | Ser | Val | Tyr | Val | Ala |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Arg | Leu | Asp | Gly | Arg | Leu | Ala | Arg | Cys | Ile | Ala | Arg | Lys | Asp | Pro | Arg |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Ala | Phe | Gly | Trp | Gln | Leu | Leu | Gln | Trp | Leu | Leu | Ile | Ala | Leu | Pro | Ala |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Thr | Phe | Val | Asn | Ser | Ala | Ile | Arg | Tyr | Leu | Glu | Gly | Gln | Leu | Ala | Leu |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Ser | Phe | Arg | Ser | Arg | Leu | Val | Ala | His | Ala | Tyr | Arg | Leu | Tyr | Phe | Ser |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Gln | Gln | Thr | Tyr | Tyr | Arg | Val | Ser | Asn | Met | Asp | Gly | Arg | Leu | Arg | Asn |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Pro | Asp | Gln | Ser | Leu | Thr | Glu | Asp | Val | Val | Ala | Phe | Ala | Ala | Ser | Val |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Ala | His | Leu | Tyr | Ser | Asn | Leu | Thr | Lys | Pro | Leu | Leu | Asp | Val | Ala | Val |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Thr | Ser | Tyr | Thr | Leu | Leu | Arg | Ala | Ala | Arg | Ser | Arg | Gly | Ala | Gly | Thr |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Ala | Trp | Pro | Ser | Ala | Ile | Ala | Gly | Leu | Val | Val | Phe | Leu | Thr | Ala | Asn |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Val | Leu | Arg | Ala | Phe | Ser | Pro | Lys | Phe | Gly | Glu | Leu | Val | Ala | Glu | Glu |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Ala | Arg | Arg | Lys | Gly | Glu | Leu | Arg | Tyr | Met | His | Ser | Arg | Val | Val | Ala |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Asn | Ser | Glu | Glu | Ile | Ala | Phe | Tyr | Gly | Gly | His | Glu | Val | Glu | Leu | Ala |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Leu | Leu | Gln | Arg | Ser | Tyr | Gln | Asp | Leu | Ala | Ser | Gln | Ile | Asn | Leu | Ile |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Leu | Leu | Glu | Arg | Leu | Trp | Tyr | Val | Met | Leu | Glu | Gln | Phe | Leu | Met | Lys |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Tyr | Val | Trp | Ser | Ala | Ser | Gly | Leu | Leu | Met | Val | Ala | Val | Pro | Ile | Ile |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Thr | Ala | Thr | Gly | Tyr | Ser | Glu | Ser | Asp | Ala | Glu | Ala | Val | Lys | Lys | Ala |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

| Ala | Leu | Glu | Lys | Lys | Glu | Glu | Glu | Leu | Val | Ser | Glu | Arg | Thr | Glu | Ala |
|-----|-----|-----|-----|-----|-----|-----|-----|-----|-----|-----|-----|-----|-----|-----|-----|
|     | 370 |     |     |     |     | 375 |     |     |     |     | 380 |     |     |     |     |

| Phe | Thr | Ile | Ala | Arg | Asn | Leu | Leu | Thr | Ala | Ala | Ala | Asp | Ala | Ile | Glu |
|-----|-----|-----|-----|-----|-----|-----|-----|-----|-----|-----|-----|-----|-----|-----|-----|
| 385 |     |     |     |     | 390 |     |     |     |     | 395 |     |     |     |     | 400 |

| Arg | Ile | Met | Ser | Ser | Tyr | Lys | Glu | Val | Thr | Glu | Leu | Ala | Gly | Tyr | Thr |
|-----|-----|-----|-----|-----|-----|-----|-----|-----|-----|-----|-----|-----|-----|-----|-----|
|     |     |     |     | 405 |     |     |     |     | 410 |     |     |     |     | 415 |     |

```
Ala Arg Val His Glu Met Phe Gln Val Phe Glu Asp Val Gln Arg Cys
            420                 425                 430

His Phe Lys Arg Pro Arg Glu Leu Glu Asp Ala Gln Ala Gly Ser Gly
            435                 440                 445

Thr Ile Gly Arg Ser Gly Val Arg Val Glu Gly Pro Leu Lys Ile Arg
        450                 455                 460

Gly Gln Val Val Asp Val Glu Gln Gly Ile Ile Cys Glu Asn Ile Pro
465                 470                 475                 480

Ile Val Thr Pro Ser Gly Glu Val Val Ala Ser Leu Asn Ile Arg
                485                 490                 495

Val Glu Glu Gly Met His Leu Leu Ile Thr Gly Pro Asn Gly Cys Gly
            500                 505                 510

Lys Ser Ser Leu Phe Arg Ile Leu Gly Gly Leu Trp Pro Thr Tyr Gly
        515                 520                 525

Gly Val Leu Tyr Lys Pro Pro Pro Gln Arg Met Phe Tyr Ile Pro Gln
    530                 535                 540

Arg Pro Tyr Met Ser Val Gly Ser Leu Arg Asp Gln Val Ile Tyr Pro
545                 550                 555                 560

Asp Ser Val Glu Asp Met Gln Arg Lys Gly Tyr Ser Glu Gln Asp Leu
                565                 570                 575

Glu Ala Ile Leu Asp Val Val His Leu His His Ile Leu Gln Arg Glu
            580                 585                 590

Gly Gly Trp Glu Ala Met Cys Asp Trp Lys Asp Val Leu Ser Gly Gly
        595                 600                 605

Glu Lys Gln Arg Ile Gly Met Ala Arg Met Phe Tyr His Arg Pro Lys
    610                 615                 620

Tyr Ala Leu Leu Asp Glu Cys Thr Ser Ala Val Ser Ile Asp Val Glu
625                 630                 635                 640

Gly Lys Ile Phe Gln Ala Ala Lys Asp Ala Gly Ile Ala Leu Leu Ser
                645                 650                 655

Ile Thr His Arg Pro Ser Leu Trp Lys Tyr His Thr His Leu Leu Gln
        660                 665                 670

Phe Asp Gly Glu Gly Gly Trp Lys Phe Glu Lys Leu Asp Ser Ala Ala
    675                 680                 685

Arg Leu Ser Leu Thr Glu Glu Lys Gln Arg Leu Glu Gln Gln Leu Ala
690                 695                 700

Gly Ile Pro Lys Met Gln Arg Arg Leu Gln Glu Leu Cys Gln Ile Leu
705                 710                 715                 720

Gly Glu Ala Val Ala Pro Ala His Val Pro Ala Pro Ser Pro Gln Gly
                725                 730                 735

Pro Gly Gly Leu Gln Gly Ala Ser Thr
            740                 745
```

( 2 ) INFORMATION FOR SEQ ID NO:3:

( i ) SEQUENCE CHARACTERISTICS:
        ( A ) LENGTH: 659 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Ala Ala Phe Ser Lys Tyr Leu Thr Ala Arg Asn Ser Ser Leu Ala
1               5                   10                  15

Gly Ala Ala Phe Leu Leu Leu Cys Leu Leu His Lys Arg Arg Arg Ala
            20                  25                  30
```

-continued

| | | | | | | | | | | | | | | |
|---|---|---|---|---|---|---|---|---|---|---|---|---|---|---|
| Leu | Gly | Leu | His | Gly | Lys | Lys | Ser | Gly | Lys | Pro | Pro | Leu | Gln | Asn | Asn |
| | | 35 | | | | | 40 | | | | 45 | | | |
| Glu | Lys | Glu | Gly | Lys | Lys | Glu | Arg | Ala | Val | Val | Asp | Lys | Val | Phe | Phe |
| | 50 | | | | | 55 | | | | 60 | | | | |
| Ser | Arg | Leu | Ile | Gln | Ile | Leu | Lys | Ile | Met | Val | Pro | Arg | Thr | Phe | Cys |
| 65 | | | | 70 | | | | | 75 | | | | | 80 |
| Lys | Glu | Thr | Gly | Tyr | Leu | Val | Leu | Ile | Ala | Val | Met | Leu | Val | Ser | Arg |
| | | | | 85 | | | | | 90 | | | | 95 | |
| Thr | Tyr | Cys | Asp | Val | Trp | Met | Ile | Gln | Asn | Gly | Thr | Leu | Ile | Glu | Ser |
| | | | 100 | | | | | 105 | | | | | 110 | |
| Gly | Ile | Ile | Gly | Arg | Ser | Arg | Lys | Asp | Phe | Lys | Arg | Tyr | Leu | Leu | Asn |
| | | 115 | | | | | 120 | | | | | 125 | | |
| Phe | Ile | Ala | Ala | Met | Pro | Leu | Ile | Ser | Leu | Val | Asn | Asn | Phe | Leu | Lys |
| | 130 | | | | | 135 | | | | | 140 | | | |
| Tyr | Gly | Leu | Asn | Glu | Leu | Lys | Leu | Cys | Phe | Arg | Val | Arg | Leu | Thr | Lys |
| 145 | | | | | 150 | | | | | 155 | | | | 160 |
| Tyr | Leu | Tyr | Glu | Glu | Tyr | Leu | Gln | Ala | Phe | Thr | Tyr | Tyr | Lys | Lys | Gly |
| | | | | 165 | | | | | 170 | | | | | 175 |
| Asn | Leu | Asp | Asn | Arg | Ile | Ala | Asn | Pro | Asp | Gln | Leu | Leu | Thr | Gln | Asp |
| | | | 180 | | | | | 185 | | | | | 190 | |
| Val | Glu | Lys | Phe | Cys | Asn | Ser | Val | Val | Asp | Leu | Tyr | Ser | Asn | Leu | Ser |
| | | 195 | | | | | 200 | | | | | 205 | | |
| Lys | Pro | Phe | Leu | Asp | Ile | Val | Leu | Tyr | Ile | Phe | Lys | Leu | Thr | Ser | Ala |
| | 210 | | | | | 215 | | | | | 220 | | | |
| Ile | Gly | Ala | Gln | Gly | Pro | Ala | Ser | Met | Met | Ala | Tyr | Leu | Val | Val | Ser |
| 225 | | | | | 230 | | | | | 235 | | | | | 240 |
| Gly | Leu | Phe | Leu | Thr | Arg | Leu | Arg | Arg | Pro | Ile | Gly | Lys | Met | Thr | Ile |
| | | | | 245 | | | | | 250 | | | | | 255 |
| Thr | Glu | Gln | Lys | Tyr | Glu | Gly | Glu | Tyr | Arg | Tyr | Val | Asn | Ser | Arg | Leu |
| | | | 260 | | | | | 265 | | | | | 270 | |
| Ile | Thr | Asn | Ser | Glu | Glu | Ile | Ala | Phe | Tyr | Asn | Gly | Asn | Lys | Arg | Glu |
| | | 275 | | | | | 280 | | | | | 285 | | |
| Lys | Gln | Thr | Val | His | Ser | Val | Phe | Arg | Lys | Leu | Val | Glu | His | Leu | His |
| | 290 | | | | | 295 | | | | | 300 | | | |
| Asn | Phe | Ile | Leu | Phe | Arg | Phe | Ser | Met | Gly | Phe | Ile | Asp | Ser | Ile | Ile |
| 305 | | | | | 310 | | | | | 315 | | | | | 320 |
| Ala | Lys | Tyr | Leu | Ala | Thr | Val | Val | Gly | Tyr | Leu | Val | Val | Ser | Arg | Pro |
| | | | | 325 | | | | | 330 | | | | | 335 |
| Phe | Leu | Asp | Leu | Ser | His | Pro | Arg | His | Leu | Lys | Ser | Thr | His | Ser | Glu |
| | | | 340 | | | | | 345 | | | | | 350 | |
| Leu | Leu | Glu | Asp | Tyr | Tyr | Gln | Ser | Gly | Arg | Met | Leu | Leu | Arg | Met | Ser |
| | | 355 | | | | | 360 | | | | | 365 | | |
| Gln | Ala | Leu | Gly | Arg | Ile | Val | Leu | Ala | Gly | Arg | Glu | Met | Thr | Arg | Leu |
| | 370 | | | | | 375 | | | | | 380 | | | |
| Ala | Gly | Phe | Thr | Ala | Arg | Ile | Thr | Glu | Leu | Met | Gln | Val | Leu | Lys | Asp |
| 385 | | | | | 390 | | | | | 395 | | | | | 400 |
| Leu | Asn | His | Gly | Lys | Tyr | Glu | Arg | Thr | Met | Val | Ser | Gln | Gln | Glu | Lys |
| | | | | 405 | | | | | 410 | | | | | 415 |
| Gly | Ile | Glu | Gly | Val | Gln | Val | Ile | Pro | Leu | Ile | Pro | Gly | Ala | Gly | Glu |
| | | | 420 | | | | | 425 | | | | | 430 | |
| Ile | Ile | Ile | Ala | Asp | Asn | Ile | Ile | Lys | Phe | Asp | His | Val | Pro | Leu | Ala |
| | | 435 | | | | | 440 | | | | | 445 | | |
| Thr | Pro | Asn | Gly | Asp | Val | Leu | Ile | Arg | Asp | Leu | Asn | Phe | Glu | Val | Arg |

|  |  |  | 450 |  |  |  |  | 455 |  |  |  | 460 |  |  |
|---|---|---|---|---|---|---|---|---|---|---|---|---|---|---|---|

| Ser | Gly | Ala | Asn | Val | Leu | Ile | Cys | Gly | Pro | Asn | Gly | Cys | Gly | Lys | Ser |
|-----|-----|-----|-----|-----|-----|-----|-----|-----|-----|-----|-----|-----|-----|-----|-----|
| 465 |     |     |     |     | 470 |     |     |     |     | 475 |     |     |     |     | 480 |
| Ser | Leu | Phe | Arg | Val | Leu | Gly | Glu | Leu | Trp | Pro | Leu | Phe | Gly | Gly | Arg |
|     |     |     |     | 485 |     |     |     |     | 490 |     |     |     |     | 495 |     |
| Leu | Thr | Lys | Pro | Glu | Arg | Arg | Lys | Leu | Phe | Tyr | Val | Pro | Gln | Arg | Pro |
|     |     |     | 500 |     |     |     |     | 505 |     |     |     |     | 510 |     |     |
| Tyr | Met | Thr | Leu | Gly | Thr | Leu | Arg | Asp | Gln | Val | Ile | Tyr | Pro | Asp | Gly |
|     |     | 515 |     |     |     |     | 520 |     |     |     |     | 525 |     |     |     |
| Arg | Glu | Asp | Gln | Lys | Arg | Lys | Gly | Ile | Ser | Asp | Leu | Val | Gln | Lys | Glu |
|     | 530 |     |     |     |     | 535 |     |     |     |     | 540 |     |     |     |     |
| Tyr | Leu | Asp | Asn | Val | Gln | Leu | Gly | His | Ile | Leu | Glu | Arg | Glu | Gly | Gly |
| 545 |     |     |     |     | 550 |     |     |     |     | 555 |     |     |     |     | 560 |
| Trp | Asp | Ser | Val | Gln | Asp | Trp | Met | Asp | Val | Leu | Ser | Gly | Gly | Glu | Lys |
|     |     |     |     | 565 |     |     |     |     | 570 |     |     |     |     | 575 |     |
| Gln | Arg | Met | Ala | Met | Ala | Arg | Leu | Phe | Tyr | His | Lys | Pro | Gln | Phe | Ala |
|     |     |     | 580 |     |     |     |     | 585 |     |     |     |     | 590 |     |     |
| Ile | Leu | Asp | Glu | Cys | Thr | Ser | Ala | Val | Ser | Val | Asp | Val | Glu | Gly | Tyr |
|     |     | 595 |     |     |     |     | 600 |     |     |     |     | 605 |     |     |     |
| Ile | Tyr | Ser | His | Cys | Arg | Lys | Val | Gly | Ile | Thr | Leu | Phe | Thr | Val | Ser |
|     |     | 610 |     |     |     |     | 615 |     |     |     |     | 620 |     |     |     |
| His | Arg | Lys | Ser | Leu | Trp | Lys | His | His | Glu | Tyr | Tyr | Leu | His | Met | Asp |
| 625 |     |     |     |     | 630 |     |     |     |     | 635 |     |     |     |     | 640 |
| Gly | Arg | Gly | Asn | Tyr | Glu | Phe | Lys | Gln | Ile | Thr | Glu | Asp | Thr | Val | Glu |
|     |     |     |     | 645 |     |     |     |     | 650 |     |     |     |     | 655 |     |
| Phe | Gly | Ser |     |     |     |     |     |     |     |     |     |     |     |     |     |

( 2 ) INFORMATION FOR SEQ ID NO:4:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
AGGTGGGGCA GGTTGGGGTG CCGGGCACGG AGGGAAGCGT GTGGCAGGGA GGCCCGGGGG        60
CAGGCAGCCG TGAGCGGTGG GGACAGTCTG GGGCGGGCCG GGGCTGATGC CAAAGGTGTG       120
GGCAGGCCAT GGGAGAGCCG GGCTGGGGTG GG                                    152
```

( 2 ) INFORMATION FOR SEQ ID NO:5:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CACCCAATCG TAACCTCTGG CTCTCGGCCT TCTGATGGCC ACCATGGCAC AGCGTGTGTG        60
AGTGGCACTG GGAGACCCTG ACCATCGCCC CCACGGGAGC TGCCCCTGTG CATGGCCAGG       120
AAGCCTCTCT GTGTCTGTCA CCCCCCGCAG GT                                    152
```

( 2 ) INFORMATION FOR SEQ ID NO:6:

( i ) SEQUENCE CHARACTERISTICS:
    ( A ) LENGTH: 152 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

```
AGGTGAGACC CAGGGCTCCA AGAGGATCCA GGCCAGGGGC CTGTCCCCCA TACCGCTGGG     60
TGCTGAGCTC ACGAGGGCCC AACTCAGCCA GCCCGCCGCC CACTTCTGCT GCCGGGGCCA    120
CCGAGGCCCT GCTGCCAGCC TTGATGCTTT CA                                  152
```

( 2 ) INFORMATION FOR SEQ ID NO:7:

( i ) SEQUENCE CHARACTERISTICS:
    ( A ) LENGTH: 152 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

```
GCACATAGAG AGAAAGAGAG AGAGAGCTGG TTGCCCCGGC ACCATTTGCA GAAGAGCCTC     60
GCCTTTCTCT CCAGCGGCTC ATTTTTGACT TTCCGCTGTC TCTGCCCTGC CCCTCCCCGC    120
CCCGCCACCC ACCCCTCTGG GGCTTTGCAG AT                                  152
```

( 2 ) INFORMATION FOR SEQ ID NO:8:

( i ) SEQUENCE CHARACTERISTICS:
    ( A ) LENGTH: 97 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

```
AGGAGGTACC CCTGGCCCAG CCCCACCCTT GCCATCCTTG CCATGCTTCT CTCCCTGCAA     60
CTGGCAGGGG CTGAGCCAGG GTCACCCTCC CTCAGGT                              97
```

( 2 ) INFORMATION FOR SEQ ID NO:9:

( i ) SEQUENCE CHARACTERISTICS:
    ( A ) LENGTH: 152 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

```
AGGTAAGGCT GTCCCCTCCC TATGAGTGAC CCCGCCCCTG CTGCTGCTGC AGGTGCTGAC     60
CTGCTGCCCC AGCTCCTCCT ATTCCCGCTC CCTCACTCAG GGACCTCCAT GTGCTTCTGG    120
CCCATCCCAG TCCACCCAGG ACGGGAGGGC TG                                  152
```

( 2 ) INFORMATION FOR SEQ ID NO:10:

( i ) SEQUENCE CHARACTERISTICS:
    ( A ) LENGTH: 152 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

| CTGGACCACA | GGCTGCTGGT | CAGGAACCAG | CTGGCATGCT | GCCAGGGATG | GGAATGAGGG | 60 |
| CGTGCAGCCA | GGGGCACGCA | GACTCCCCAG | AATGCAGAGG | GGTCGCCACC | ACTCCCTCTC | 120 |
| CACCCCAGCC | CCGCTGTGCT | GTCTCTGCAG | GC | | | 152 |

( 2 ) INFORMATION FOR SEQ ID NO:11:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

| GGGTAGGTCC | AGCGGGGAGG | GCGCCAGCCA | CGCACATATG | CAAGCCTCAG | CCCTTGGCTT | 60 |
| CCCGCCTGTC | TGTGCTGGCA | ACAGCCATTG | TCCCTAGATG | TACGTGGCAG | GTGGGCCAAG | 120 |
| GTCAAGGTGA | GAGACCAACG | TGTCTCTGAC | TG | | | 152 |

( 2 ) INFORMATION FOR SEQ ID NO:12:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

| TCCCCCAGGC | CTGCTGTCC | CTTATCAAGA | GATCAAGAAT | GGCCTGCGTG | CTGGCCTCGG | 60 |
| GCATTGGGAG | CCTCTCAAGG | CTGGTCAGGA | GGCCATAGGG | TACGGGAAGG | GGCCTGCGCT | 120 |
| CTCTGGCGTC | AGCGGCTGTT | GCCCCTGCAG | GT | | | 152 |

( 2 ) INFORMATION FOR SEQ ID NO:13:

( i ) SEQUENCE CHARACTERISTICS:
        ( A ) LENGTH: 340 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

| AGGTAAGGAA | GCCCGTGCGC | CTCTCCTCCA | CCTCTTCCTG | CCTGTGCGCT | CACACATGGC | 60 |
| TTCCTGCAGA | GGCCCAGGAA | GTGGTGAAGA | GTCAGCACCT | CAGGAGAGGA | CACTGAGGCA | 120 |
| CTGTCCCCAG | AGCCAGAGAC | GGGCTGTGGT | TCCTGCTCCC | TCCAAACCCG | CCCGATCCAC | 180 |
| TGCCCTGTTT | TGGATCTGTG | TGGGGTGTGT | GCACGGGCGG | CGATGTGAGC | GTGTGGATGC | 240 |
| GTGTGAGCGT | GGCATGTGGA | CACTGCCTGG | GAGGCGCAGA | GTATCTTGGG | GGAGGCAGAG | 300 |
| CCGGCCCTTC | CCTCCGTGGA | CACCCAGCTT | TCCCACAGGC | | | 340 |

( 2 ) INFORMATION FOR SEQ ID NO:14:

( i ) SEQUENCE CHARACTERISTICS:
        ( A ) LENGTH: 152 base pairs
        ( B ) TYPE: nucleic acid (C) STRANDEDNESS: single
        (D) TOPOLOGY: linear (i i) MOLECULE TYPE: DNA (genomic)

(x i) SEQUENCE DESCRIPTION: SEQ ID NO:14:

| | | | | | |
|---|---|---|---|---|---|
| AGGTAGGAGG | CCTGGGGCTG | GCAGCCACCC | TTTGTCCCAC | CCTGGCCTCT | CCCTTGGCCT | 60
| CCAGGGAGTG | AAGATTACCT | CAACATCCAG | AGTCTAAAGT | GCCAGGTGCC | ACGGGGCGGG | 120
| GCAGAGGCTG | CTACCAGGGA | GGACCAACAC | CA | | | 152

(2) INFORMATION FOR SEQ ID NO:15:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:15:

| | | | | | |
|---|---|---|---|---|---|
| ATGATTAATG | CCTGTCAGAC | AGACAAGGAC | GCAGAGGCAC | AGGGGCCCTG | TCGTCACAGC | 60
| TAGCTCATTC | CCGCAGCTCC | CCCAGCTCCC | CGGCTGGCCC | CCGGGTCTGG | GTGCTGGTGG | 120
| AACTGAGCCA | AGACCATTGC | CCCCGCCTAG | GT | | | 152

(2) INFORMATION FOR SEQ ID NO:16:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:16:

| | | | | | |
|---|---|---|---|---|---|
| AGGTGAGCAC | TCCGGACCGG | CAGGCTCCCT | GGGGTCCCCT | GGAAGGGGAA | GTAGCAGCTG | 60
| TGGGGAGGCC | TGGGCTCAGT | GGAGCCTGAG | CCGGGCTGGG | GTGTTGGGCC | CTGGAGGGTG | 120
| CACAGACTCT | CCTCTCGGCC | CGGACCCCA | GGC | | | 153

(2) INFORMATION FOR SEQ ID NO:17:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:17:

| | | | | | |
|---|---|---|---|---|---|
| TGGTAGGTGC | CCTGTCTCCC | TGCCTGGGGT | CGGTGGGAGT | GCCTGCCTGA | GGGGAGGAGG | 60
| TGGCCTGGCG | GGCCCGGCAG | CAGCAGGCGG | CTGTCATCAG | CAGCCCCGT | GCCGTGCCCC | 120
| TGACCCTGTC | CCTCTCCTGG | CCAGGA | | | | 146

(2) INFORMATION FOR SEQ ID NO:18:

(i) SEQUENCE CHARACTERISTICS:
        (A) LENGTH: 1441 base pairs
        (B) TYPE: nucleic acid
        (C) STRANDEDNESS: single
        (D) TOPOLOGY: linear (i i) MOLECULE TYPE: DNA (genomic)

( x i ) SEQUENCE DESCRIPTION: SEQ ID NO:18:

| | | | | | |
|---|---|---|---|---|---|
| GCGGAGCGGA | CGGACGCGCC | TGGTGCCCCG | GGGAGGGGCG | CCACCGGGGG | AGGAGGAGGA | 60
| GGAGAAGGTG | GAGAGGAAGA | GACGCCCCCT | CTGCCCGAGA | CCTCTCAAGG | CCCTGACCTC | 120
| AGGGGCCAGG | GCACTGACAG | GACAGGAGAG | CCAAGTTCCT | CCACTTGGGC | TGCCCGAAGA | 180
| GGCCGCGACC | CTGGAGGGCC | CTGAGCCCAC | CGCACCAGGG | GCCCCAGCAC | CACCCCGGGG | 240
| GCCTAAAGCG | ACAGTCTCAG | GGGCCATCGC | AAGGTTTCCA | GTTGCCTAGA | CAACAGGCCC | 300
| AGGGTCAGAG | CAACAATCCT | TCCAGCCACC | TGCCTCAACT | GCTGCCCCAG | GCACCAGCCC | 360
| CAGTCCCTAC | GCGGCAGCCA | GCCCAGGTGA | CATGCCGGTG | CTCTCCAGGC | CCCGGCCCTG | 420
| GCGGGGGAAC | ACGCTGAAGC | GCACGGCCGT | GCTCCTGGCC | CTCGCGGCCT | ATGGAGCCCA | 480
| CAAAGTCTAC | CCCTTGGTGC | GCCAGTGCCT | GGCCCCGGCC | AGGGGTCTTC | AGGCGCCCGC | 540
| CGGGGAGCCC | ACGCAGGAGG | CCTCCGGGGT | CGCGGCGGCC | AAAGCTGGCA | TGAACCGGGT | 600
| ATTCCTGCAG | CGGCTCCTGT | GGCTCCTGCG | GCTGCTGTTC | CCCCGGGTCC | TGTGCCGGGA | 660
| GACGGGGCTG | CTGGCCCTGC | ACTCGGCCGC | CTTGGTGAGC | CGCACCTTCC | TGTCGGTGTA | 720
| TGTGGCCCGC | CTGGACGGAA | GGCTGGCCCG | CTGCATCGCC | CGCAAGGACC | CGCGGGCTTT | 780
| TGGCTGGCAG | CTGCTGCAGT | GGCTCCTCAT | CGCCCTCCCT | GCTACCTTCG | TCAACAGTGC | 840
| CATCCGTTAC | CTGGAGGGCC | AACTGGCCCT | GTCGTTCCGC | AGCCGTCTGG | TGGCCCACGC | 900
| CTACCGCCTC | TACTTCTCCC | AGCAGACCTA | CTACCGGGTC | AGCAACATGG | ACGGGCGGCT | 960
| TCGCAACCCT | GACCAGTCTC | TGACGGAGGA | CGTGGTGGCC | TTTGCGGCCT | CTGTGGCCCA | 1020
| CCTCTACTCC | AACCTGACCA | AGCCACTCCT | GGACGTGGCT | GTGACTTCCT | ACACCCTGCT | 1080
| TCGGGCGGCC | CGCTCCCGTG | GAGCCGGCAC | AGCCTGGCCC | TCGGCCATCG | CCGGCCTCGT | 1140
| GGTGTTCCTC | ACGGCCAACG | TGCTGCGGGC | CTTCTCGCCC | AAGTTCGGGG | AGCTGGTGGC | 1200
| AGAGGAGGCG | CGGCGGAAGG | GGGAGCTGCG | CTACATGCAC | TCGCGTGTGG | TGGCCAACTC | 1260
| GGAGGAGATC | GCCTTCTATG | GGGGCCATGA | GGTGGGGCAG | GTTGGGGTGC | CGGGCACGGA | 1320
| GGGAAGCGTG | TGGCAGGGAG | GCCCGGGGGC | AGGCAGCCGT | GAGCGGTGGG | GACAGTCTGG | 1380
| GGCGGGCCGG | GGCTGATGCC | AAAGGTGTGG | GCAGGCCATG | GGAGAGCCGG | GCTGGGGTGG | 1440
| G | | | | | | 1441

( 2 ) INFORMATION FOR SEQ ID NO:19:

( i ) SEQUENCE CHARACTERISTICS:
        ( A ) LENGTH: 481 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

| | | | | | |
|---|---|---|---|---|---|
| CACCCAATCG | TAACCTCTGG | CTCTCGGCCT | TCTGATGGCC | ACCATGGCAC | AGCGTGTGTG | 60
| AGTGGCACTG | GGAGACCCTG | ACCATCGCCC | CCACGGGAGC | TGCCCCTGTG | CATGGCCAGG | 120
| AAGCCTCTCT | GTGTCTGTCA | CCCCCCGCAG | GTGGAGCTGG | CCCTGCTACA | GCGCTCCTAC | 180
| CAGGACCTGG | CCTCGCAGAT | CAACCTCATC | CTTCTGGAAC | GCCTGTGGTA | TGTTATGCTG | 240
| GAGCAGTTCC | TCATGAAGTA | TGTGTGGAGC | GCCTCGGGCC | TGCTCATGGT | GGCTGTCCCC | 300
| ATCATCACTG | CCACTGGCTA | CTCAGAGTCA | GGTGAGACCC | AGGGCTCCAA | GAGGATCCAG | 360
| GCCAGGGGCC | TGTCCCCCAT | ACCGCTGGGT | GCTGAGCTCA | CGAGGGCCCA | ACTCAGCCAG | 420

| CCCGCCGCCC | ACTTCTGCTG | CCGGGGCCAC | CGAGGCCCTG | CTGCCAGCCT | TGATGCTTTC | 480 |
| A | | | | | | 481 |

( 2 ) INFORMATION FOR SEQ ID NO:20:

( i ) SEQUENCE CHARACTERISTICS:
        ( A ) LENGTH: 702 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

| GCACATAGAG | AGAAAGAGAG | AGAGAGCTGG | TTGCCCCGGC | ACCATTTGCA | GAAGAGCCTC | 60 |
| GCCTTTCTCT | CCAGCGGCTC | ATTTTTGACT | TTCCGCTGTC | TCTGCCCTGC | CCCTCCCCGC | 120 |
| CCCGCCACCC | ACCCCTCTGG | GGCTTTGCAG | ATGCAGAGGC | CGTGAAGAAG | GCAGCCTTGG | 180 |
| AAAAGAAGGA | GGAGGAGCTG | GTGAGCGAGC | GCACAGAAGC | CTTCACTATT | GCCCGCAACC | 240 |
| TCCTGACAGC | GGCTGCAGAT | GCCATTGAGC | GGATCATGTC | GTCGTACAAG | GAGGTACCCC | 300 |
| TGGCCCAGCC | CCACCCTTGC | CATCCTTGCC | ATGCTTCTCT | CCCTGCAACT | GGCAGGGGCT | 360 |
| GAGCCAGGGT | CACCCTCCCT | CAGGTGACGG | AGCTGGCTGG | CTACACAGCC | CGGGTGCACG | 420 |
| AGATGTTCCA | GGTATTTGAA | GATGTTCAGC | GCTGTCACTT | CAAGAGGCCC | AGGGAGCTAG | 480 |
| AGGACGCTCA | GGCGGGGTCT | GGGACCATAG | GCCGGTCTGG | TGTCCGTGTG | GAGGGCCCCC | 540 |
| TGAAGATCCG | AGGTAAGGCT | GTCCCTCCC | TATGAGTGAC | CCCGCCCCTG | CTGCTGCTGC | 600 |
| AGGTGCTGAC | CTGCTGCCCC | AGCTCCTCCT | ATTCCCGCTC | CCTCACTCAG | GGACCTCCAT | 660 |
| GTGCTTCTGG | CCCATCCCAG | TCCACCCAGG | ACGGGAGGGC | TG | | 702 |

( 2 ) INFORMATION FOR SEQ ID NO:21:

( i ) SEQUENCE CHARACTERISTICS:
        ( A ) LENGTH: 395 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

| CTGGACCACA | GGCTGCTGGT | CAGGAACCAG | CTGGCATGCT | GCCAGGGATG | GGAATGAGGG | 60 |
| CGTGCAGCCA | GGGGCACGCA | GACTCCCCAG | AATGCAGAGG | GGTCGCCACC | ACTCCCTCTC | 120 |
| CACCCCAGCC | CCGCTGTGCT | GTCTCTGCAG | GCCAGGTGGT | GGATGTGGAA | CAGGGGATCA | 180 |
| TCTGCGAGAA | CATCCCCATC | GTCACGCCCT | CAGGAGAGGT | GGTGGTGGCC | AGCCTCAACA | 240 |
| TCAGGGTAGG | TCCAGCGGGG | AGGGCGCCAG | CCACGCACAT | ATGCAAGCCT | CAGCCCTTGG | 300 |
| CTTCCCGCCT | GTCTGTGCTG | GCAACAGCCA | TTGTCCCTAG | ATGTACGTGG | CAGGTGGGCC | 360 |
| AAGGTCAAGG | TGAGAGACCA | ACGTGTCTCT | GACTG | | | 395 |

( 2 ) INFORMATION FOR SEQ ID NO:22:

( i ) SEQUENCE CHARACTERISTICS:
        ( A ) LENGTH: 928 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
TCCCCCAGGC CCTGCTGTCC CTTATCAAGA GATCAAGAAT GGCCTGCGTG CTGGCCTCGG    60
GCATTGGGAG CCTCTCAAGG CTGGTCAGGA GGCCATAGGG TACGGGAAGG GGCCTGCGCT   120
CTCTGGCGTC AGCGGCTGTT GCCCCTGCAG GTGGAGGAAG GCATGCATCT GCTCATCACA   180
GGCCCCAATG GCTGCGGCAA GAGCTCCCTG TTCCGGATCC TGGGTGGGCT CTGGCCCACG   240
TACGGTGGTG TGCTCTACAA GCCCCCACCC CAGCGCATGT CTACATCCC  GCAGAGGTAA   300
GGAAGCCCGT GCGCCTCTCC TCCACCTCTT CCTGCCTGTG CGCTCACACA TGGCTTCCTG   360
CAGAGGCCCA GGAAGTGGTG AAGAGTCAGC ACCTCAGGAG AGGACACTGA GGCACTGTCC   420
CCAGAGCCAG AGACGGGCTG TGGTTCCTGC TCCCTCCAAA CCCGCCCGAT CCACTGCCCT   480
GTTTTGGATC TGTGTGGGGT GTGTGCACGG CGGCGATGT  GAGCGTGTGG ATGCGTGTGA   540
GCGTGGCATG TGGACACTGC CTGGGAGGCG CAGAGTATCT TGGGGGAGGC AGAGCCGGCC   600
CTTCCCTCCG TGGACACCCA GCTTTCCCAC AGGCCCTACA TGTCTGTGGG CTCCCTGCGT   660
GACCAGGTGA TCTACCCGGA CTCAGTGGAG GACATGCAAA GGAAGGGCTA CTCGGAGCAG   720
GACCTGGAAG CCATCCTGGA CGTCGTGCAC CTGCACCACA TCCTGCAGCG GGAGGGAGGT   780
AGGAGGCCTG GGCTGGCAG  CCACCCTTTG TCCCACCCTG GCCTCTCCCT TGGCCTCCAG   840
GGAGTGAAGA TTACCTCAAC ATCCAGAGTC TAAAGTGCCA GGTGCCACGG GGCGGGGCAG   900
AGGCTGCTAC CAGGGAGGAC CAACACCA                                     928
```

( 2 ) INFORMATION FOR SEQ ID NO:23:

( i ) SEQUENCE CHARACTERISTICS:
        ( A ) LENGTH: 1025 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
ATGATTAATG CCTGTCAGAC AGACAAGGAC GCAGAGGCAC AGGGGCCCTG TCGTCACAGC    60
TAGCTCATTC CCGCAGCTCC CCCAGCTCCC CGGCTGGCCC CCGGGTCTGG GTGCTGGTGG   120
AACTGAGCCA AGACCATTGC CCCCGCCTAG GTTGGGAGGC TATGTGTGAC TGGAAGGACG   180
TCCTGTCGGG TGGCGAGAAG CAGAGAATCG GCATGGCCCG CATGTTCTAC CACAGGTGAG   240
CACTCCGGAC CGGCAGGCTC CTGGGGTCC  CCTGGAAGGG GAAGTAGCAG CTGTGGGGAG   300
GCCTGGGCTC AGTGGAGCCT GAGCCGGGCT GGGGTGTTGG GCCCTGGAGG GTGCACAGAC   360
TCTCCTCTCG GCCCGGACCC CCAGGCCCAA GTACGCCCTC CTGGATGAAT GCACCAGCGC   420
CGTGAGCATC GACGTGGAAG GCAAGATCTT CCAGGCGGCC AAGGACGCGG GCATTGCCCT   480
GCTCTCCATC ACCCACCGGC CCTCCCTGTG GTAGGTGCCC TGTCTCCCTG CCTGGGGTCG   540
GTGGGAGTGC CTGCCTGAGG GGAGGAGGTG GCCTGGCGGG CCCGGCAGCA GCAGGCGGCT   600
GTCATCAGCA GCCCCGTGC  CGTGCCCCTG ACCCTGTCCC TCTCCTGGCC AGGAAATACC   660
ACACACACTT GCTACAGTTC GATGGGGAGG GCGGCTGGAA GTTCGAGAAG CTGGACTCAG   720
CTGCCCGCCT GAGCCTGACG GAGGAGAAGC AGCGGCTGGA GCAGCAGCTG GCGGGCATTC   780
CAAGATGCA  GCGGCGCCTC CAGGAGCTCT GCCAGATCCT GGGCGAGGCC GTGGCCCCAG   840
CGCATGTGCC GGCACCTAGC CCGCAAGGCC CTGGTGGCCT CCAGGGTGCC TCCACCTGAC   900
```

-continued

| | | | | | |
|---|---|---|---|---|---|
| ACAACCGTCC | CCGGCCCCTG | CCCCGCCCCC | AAGCTCGGAT | CACATGAAGG | AGACAGCAGC | 960 |
| ACCCACCCAT | GCACGCACCC | CGCCCCTGCA | TGCCTGGCCC | CTCCTCCTAG | AAAACCCTTC | 1020 |
| CCGCC | | | | | | 1025 |

We claim:

1. An isolated nucleotide sequence selected from the group consisting of a cDNA having the sequence represented in FIG. 2 (SEQ ID NO:1), an isolated genomic DNA sequence comprising said cDNA, and RNA encoding the protein of SEQ ID NO:2, said sequence being in unmutated form and which, in mutated forms, is responsible for adrenoleukodystrophy or adrenomyelopathy.

2. An isolated nucleotide sequence according to claim 1, having the sequence represented in FIG. 6 (SEQ ID NOS: 4–17) or FIG. 7 (SEQ ID NOS: 8–23).

3. An isolated DNA sequence consisting of a DNA sequence encoding the human adrenoleukodystrophy protein.

4. An isolated DNA sequence according to claim 3, consisting of the sequence represented in FIG. 2 (SEQ ID NO:1).

5. An isolated genomic DNA sequence according to claim 1, which has the restriction sites shown in FIG. 5.

* * * * *